US012040091B2

(12) United States Patent
Nenoki et al.

(10) Patent No.: US 12,040,091 B2
(45) Date of Patent: Jul. 16, 2024

(54) MEDICAL EXAMINATION SUPPORT APPARATUS, AND OPERATION METHOD AND OPERATION PROGRAM THEREOF

(71) Applicants: FUJIFILM Corporation, Tokyo (JP); FUJIFILM Medical Systems USA, Inc., Lexington, MA (US)

(72) Inventors: Yasuyo Nenoki, Tokyo (JP); Junichi Ishigaki, Tokyo (JP); Keiji Sugihara, Tokyo (JP)

(73) Assignees: FUJIFILM Corporation, Tokyo (JP); FUJIFILM Medical Systems USA, Inc., Lexington, MA (US)

( * ) Notice: Subject to any disclaimer, the term of this patent is extended or adjusted under 35 U.S.C. 154(b) by 40 days.

(21) Appl. No.: 16/878,629

(22) Filed: May 20, 2020

(65) Prior Publication Data

US 2020/0279652 A1  Sep. 3, 2020

Related U.S. Application Data

(63) Continuation of application No. PCT/JP2018/042566, filed on Nov. 16, 2018.

(30) Foreign Application Priority Data

Nov. 21, 2017 (JP) ................. 2017-223842

(51) Int. Cl.
*G16H 50/20* (2018.01)
*A61B 5/00* (2006.01)
(Continued)

(52) U.S. Cl.
CPC ............. *G16H 50/20* (2018.01); *A61B 5/743* (2013.01); *G16H 30/40* (2018.01); *G16H 40/67* (2018.01)

(58) Field of Classification Search
CPC ........ G16H 50/20; G16H 40/67; G16H 30/40; A61B 5/743
See application file for complete search history.

(56) References Cited

U.S. PATENT DOCUMENTS 5,235,510 A     8/1993 Yamada et al.
10,446,270 B2 * 10/2019 Tsugo .................... G16H 40/63
(Continued)

FOREIGN PATENT DOCUMENTS

EP    2385474     11/2011
JP    H0512352   1/1993
(Continued)

OTHER PUBLICATIONS

Garner-Thorpe, The Value of Modified Early Warning Score (MEWS) in Surgical In-Patients: A Prospective Observational Study, https://www.ncbi.nlm.nih.gov/pmc/articles/PMC1963767/#:~:text=The%20Modified%20Early%20Warning%20Score,transfer%20of%20critically%20ill%20patients. (Year: 2006).*
(Continued)

*Primary Examiner* — Aryan E Weisenfeld
(74) *Attorney, Agent, or Firm* — JCIPRNET

(57) ABSTRACT

A request receiving unit of a medical examination support server receives at least two selection instructions among a plurality of pieces of examination data obtained in a medical examination performed on a patient. An algorithm selection unit selects a suitable diagnosis support algorithm according to at least two pieces of the examination data from among the plurality of diagnosis support algorithms. An analysis processing unit performs analysis processing by the suitable diagnosis support algorithm. A screen output control unit controls an output of an information display screen including an information display region in which diagnosis support information of the suitable diagnosis support algorithm is displayed.

7 Claims, 22 Drawing Sheets

(51) Int. Cl.
*G16H 30/40* (2018.01)
*G16H 40/67* (2018.01)

(56) References Cited

U.S. PATENT DOCUMENTS

| 2007/0076934 | A1 | 4/2007 | Krishnan et al. |
| 2009/0196479 | A1 | 8/2009 | Raman et al. |
| 2016/0085928 | A1* | 3/2016 | Tsugo ............... G16H 50/20 705/2 |
| 2016/0253467 | A1 | 9/2016 | Kitagawa et al. |

FOREIGN PATENT DOCUMENTS

| JP | 2010170311 | 8/2010 |
| JP | 5175752 | 4/2013 |
| JP | 2016162131 | 9/2016 |

OTHER PUBLICATIONS

Langan, "Development and Validation of an Algorithm to Accurately Identify Atopic Eczema Patients in Primary Care Electronic Health Records from the UK" (Year: 2017).*
"Office Action of Canada Counterpart Application" issued on Oct. 21, 2021, p. 1-p. 8.
"Office Action of Australia Counterpart Application", issued on Sep. 16, 2021, p. 1-p. 3.
"International Search Report (Form PCT/ISA/210)" of PCT/JP2018/042566, mailed on Dec. 25, 2018, with English translation thereof, pp. 1-3.
"Written Opinion of the International Searching Authority (Form PCT/ISA/237)" of PCT/JP2018/042566, mailed on Dec. 25, 2018, with English translation thereof, pp. 1-7.
"Search Report of Europe Counterpart Application", issued on Dec. 2, 2020, pp. 1-8.
"Office Action of Australia Counterpart Application", issued on Mar. 10, 2022, p. 1-p. 3.
"Office Action of Australia Counterpart Application", issued on Aug. 8, 2022, pp. 1-3.
"Office Action of Canada Counterpart Application", issued on Sep. 2, 2022, p. 1-p. 5.
Office Action of Canadian Counterpart Application, issued on May 26, 2023, pp. 1-7.
"Office Action of Europe Counterpart Application", issued on Oct. 12, 2023, p. 1-p. 8.
"Office Action of Australia Counterpart Application", issued on Nov. 6, 2023, p. 1-p. 4.
"Office Action of Australia Counterpart Application", issued on Mar. 1, 2024, pp. 1-4.
"Office Action of Mexico Counterpart Application", issued on Feb. 27, 2024, with English translation thereof, pp. 1-10.

* cited by examiner

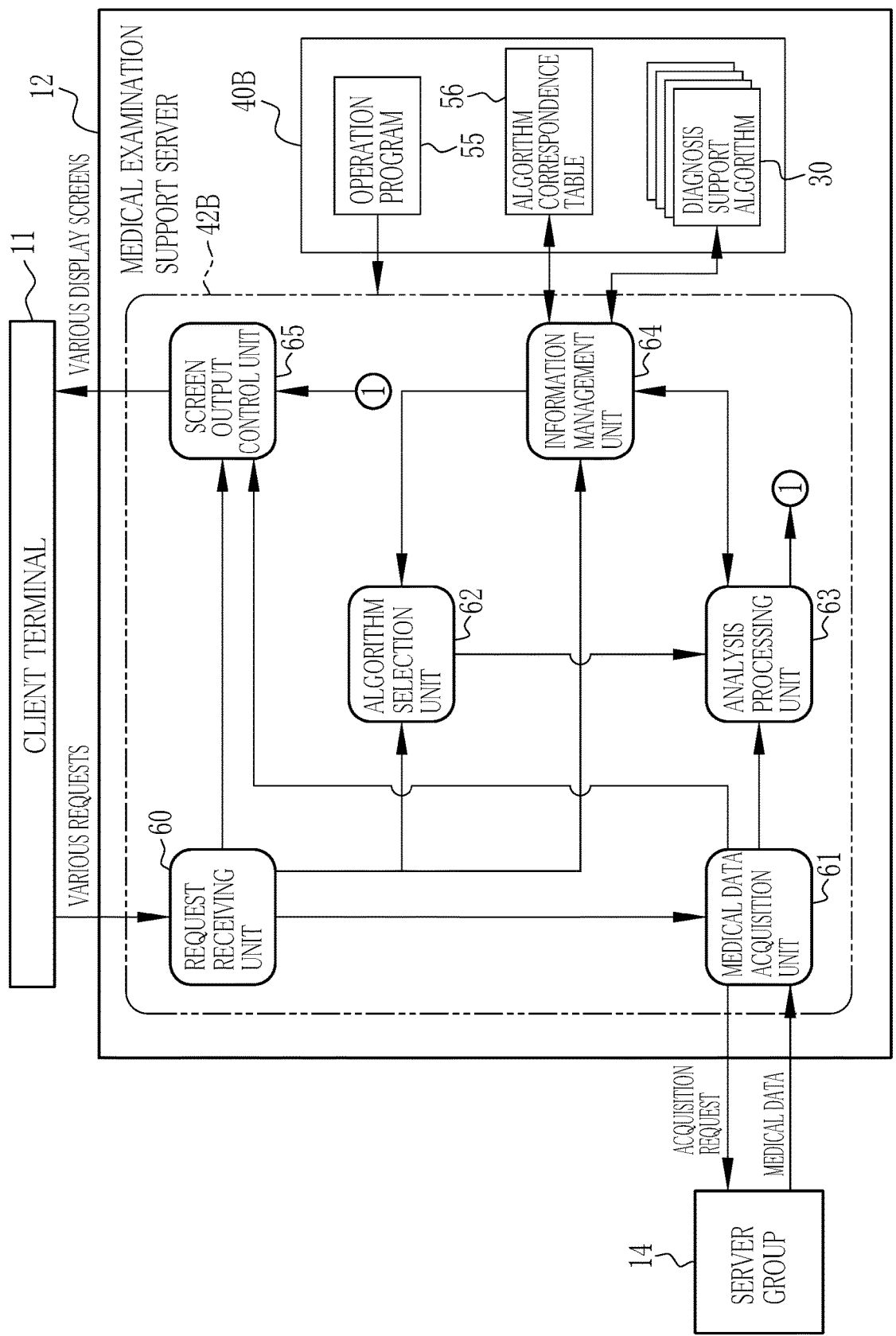

FIG.9

| ALGORITHM CORRESPONDENCE TABLE ~56 | |
|---|---|
| EXAMINATION DATA | ALGORITHM ID (OUTLINE) |
| TWO OR MORE CT IMAGES HAVING DIFFERENT IMAGING DATE AND TIME | AL001 (LESION SIZE CHANGE GRAPH CREATION) |
| TWO OR MORE HEAD CT IMAGES | AL002 (CEREBRAL INFARCTION RISK DETERMINATION) |
| TWO OR MORE HEAD CT IMAGES | AL003 (DEMENTIA RISK DETERMINATION) |
| TWO OR MORE CHEST DR IMAGES | AL004 (SHADOW TYPE DISCRIMINATION) |
| CHEST DR IMAGE, CHEST CT IMAGE | AL005 (LUNG CANCER STAGE DETERMINATION) |
| BLOOD TEST, ECG, CAG IMAGE | AL006 (HEART DISEASE DETERMINATION) |
| ANY ONE MEDICAL IMAGE, VITAL SIGN | AL007 (SIMILAR CASE IMAGE SEARCH) |

SELECTION INSTRUCTION

FIG.21

| ALGORITHM CORRESPONDENCE TABLE ~120 | | |
|---|---|---|
| EXAMINATION DATA | ALGORITHM ID (OUTLINE) | EVALUATION SCORE |
| ANY ONE MEDICAL IMAGE, VITAL SIGN, BLOOD TEST | AL050 (SIMILAR CASE IMAGE SEARCH) | 8.6 |
| ANY ONE MEDICAL IMAGE, VITAL SIGN, BLOOD TEST | AL051 (SIMILAR CASE IMAGE SEARCH) | 6.2 |
| ANY ONE MEDICAL IMAGE, VITAL SIGN, BLOOD TEST | AL052 (SIMILAR CASE IMAGE SEARCH) | 7.7 |

MEDICAL EXAMINATION SUPPORT APPARATUS, AND OPERATION METHOD AND OPERATION PROGRAM THEREOF

CROSS-REFERENCE TO RELATED APPLICATIONS

This application is a Continuation of PCT International Application No. PCT/JP2018/042566 filed on 16 Nov. 2018, which claims priority under 35 U.S.C § 119(a) to Japanese Patent Application No. 2017-223842 filed on 21 Nov. 2017. The above application is hereby expressly incorporated by reference, in its entirety, into the present application.

BACKGROUND OF THE INVENTION

1. Field of the Invention

The present invention relates to a medical examination support apparatus, and an operation method and an operation program thereof.

2. Description of the Related Art

A doctor performs various medical examinations on a patient and views and analyzes the obtained examination data by himself/herself. For example, in a case where the medical examination is an image examination such as a computed tomography (CT) examination or a magnetic resonance imaging (MM) examination, and the examination data is a medical image, a doctor views the medical image to extract a lesion shown in the medical image, identifies the type of the extracted lesion, and measures the size. In order to assist a doctor in performing diagnosis, recently, a diagnosis support algorithm which automatically performs analysis processing on the examination data and outputs a result of the analysis processing as diagnosis support information for supporting diagnosis of the doctor has been developed.

For example, there is a diagnosis support algorithm suitable for each examination data (hereinafter, referred to as a suitable diagnosis support algorithm), such as a diagnosis support algorithm A for analysis of the CT image, and a diagnosis support algorithm B for analysis of the MM image. It takes time and effort for the doctor to select the suitable diagnosis support algorithm from among a plurality of diagnosis support algorithms each time the suitable diagnosis support algorithm is used.

Therefore, in a medical examination support apparatus disclosed in JP5175752B, the time and effort for the doctor to select a suitable diagnosis support algorithm is saved by automatically selecting a suitable diagnosis support algorithm for one medical image of which a selection instruction (described as image processing request in JP5175752B) is received. In JP5175752B, image processing is performed on the medical image by the selected suitable diagnosis support algorithm, and the medical image after the image processing is displayed as diagnosis support information.

SUMMARY OF THE INVENTION

In JP5175752B, a selection instruction of one medical image is received so that the suitable diagnosis support algorithm for the medical image is selected, but in actual diagnosis, a plurality of medical images are referred to in many cases. Therefore, in JP5175752B, a case in which selection instructions of a plurality of medical images are received at one time is considered. In this case, the suitable diagnosis support algorithm is selected for each of the plurality of medical images. For example, in a case where the plurality of medical image are the CT image and the MRI image, the diagnosis support algorithms A and B are selected as the suitable diagnosis support algorithms respectively, in the above-described example. However, in a case where the CT image and the MRI image are complexly subjected to the analysis processing and there is a diagnosis support algorithm C for outputting diagnosis support information different from that of the diagnosis support algorithms A and B, the suitable diagnosis support algorithm is not always selected by the above-described simple selection method.

It is considered that a diagnosis support algorithm for a plurality of pieces of examination data such as the diagnosis support algorithm C can provide, to a doctor, more useful diagnosis support information as compared with a diagnosis support algorithm for one piece of examination data such as the diagnosis support algorithms A and B. Further, in consideration that the types of examination data are increasing with the advances in medicine that is accelerating year by year, it is expected that the demand for a diagnosis support algorithm for a plurality of pieces of examination data will continue to increase. Accordingly, even in case of a diagnosis support algorithm for a plurality of pieces of examination data, a mechanism for selecting a suitable diagnosis support algorithm without the intervention of a doctor is required.

An object of the invention is to provide a medical examination support apparatus which can select a suitable diagnosis support algorithm for a plurality of pieces of examination data without the intervention of a doctor, and an operation method and an operation program thereof.

In order to achieve the above-described object, a medical examination support apparatus according to an embodiment of the invention comprises an instruction receiving unit that receives at least two selection instructions among a plurality of pieces of examination data obtained in a medical examination performed on a patient; an algorithm selection unit that selects a suitable diagnosis support algorithm according to at least two pieces of the examination data of which the selection instructions are received by the instruction receiving unit, from among a plurality of diagnosis support algorithms for performing analysis processing on the examination data and outputting an analysis processing result as diagnosis support information for supporting diagnosis of a doctor; an analysis processing unit that performs the analysis processing by the suitable diagnosis support algorithm; and a screen output control unit that controls an output of an information display screen including an information display region in which the diagnosis support information of the suitable diagnosis support algorithm is displayed.

It is preferable that the information display screen includes a list display region in which the plurality of pieces of examination data are displayed in a list for receiving the selection instruction, in addition to the information display region, the algorithm selection unit selects the suitable diagnosis support algorithm again each time a selection state of the examination data in the list display region is changed, and in a case where the suitable diagnosis support algorithm is selected again by the algorithm selection unit so that the diagnosis support information is updated, the screen output control unit switches a display of the information display region to the updated diagnosis support information in conjunction with the change of the selection state.

It is preferable that the algorithm selection unit performs candidate extraction processing of extracting candidates for the suitable diagnosis support algorithm according to the at least two pieces of examination data, and main selection processing of selecting the suitable diagnosis support algorithm from among the candidates according to a determination criterion set in advance.

It is preferable that in a case where the instruction receiving unit receives a selection instruction of one piece of the examination data, the screen output control unit displays detailed information of the one pieces of examination data of which the selection instruction is received by the instruction receiving unit.

It is preferable that the screen output control unit switches between display and non-display of the information display region according to an operation of the doctor.

An operation method of a medical examination support apparatus according to an embodiment of the invention comprises an instruction receiving step of receiving at least two selection instructions among a plurality of pieces of examination data obtained in a medical examination performed on a patient; an algorithm selection step of selecting a suitable diagnosis support algorithm according to at least two pieces of the examination data of which the selection instruction is received in the instruction receiving step, from among a plurality of diagnosis support algorithms for performing analysis processing on the examination data and outputting an analysis processing result as diagnosis support information for supporting diagnosis of a doctor; an analysis processing step of performing the analysis processing by the suitable diagnosis support algorithm; and a screen output control step of controlling an output of an information display screen including an information display region in which the diagnosis support information of the suitable diagnosis support algorithm is displayed.

An operation program of a medical examination support apparatus according to an embodiment of the invention causes a computer to execute an instruction receiving function of receiving at least two selection instructions among a plurality of pieces of examination data obtained in a medical examination performed on a patient; an algorithm selection function of selecting a suitable diagnosis support algorithm according to at least two pieces of the examination data of which the selection instruction is received in the instruction receiving function, from among a plurality of diagnosis support algorithms for performing analysis processing on the examination data and outputting an analysis processing result as diagnosis support information for supporting diagnosis of a doctor; an analysis processing function of performing the analysis processing by the suitable diagnosis support algorithm; and a screen output control function of controlling an output of an information display screen including an information display region in which the diagnosis support information of the suitable diagnosis support algorithm is displayed.

The invention can provide a medical examination support apparatus which can select a suitable diagnosis support algorithm for a plurality of pieces of examination data without intervention of a doctor since at least two selection instructions among a plurality of pieces of examination data obtained in a medical examination performed on a patient are received and a suitable diagnosis support algorithm according to the at least two pieces of examination data is selected from among a plurality of diagnosis support algorithms, and an operation method and an operation program thereof.

BRIEF DESCRIPTION OF THE DRAWINGS

FIG. 8 is a block diagram illustrating various processing units of a CPU of the medical examination support server.

FIG. 9 is a diagram illustrating contents of an algorithm correspondence table.

FIG. 14A illustrates a state where a selection instruction of one piece of examination data is received, and FIG. 14B illustrates a viewer screen as the detailed information.

FIG. 17A illustrates an aspect before the change of the selection state, and FIG. 17B illustrates an aspect after the change of the selection state.

FIG. 21 is a diagram illustrating contents of an algorithm correspondence table of a second embodiment.

DESCRIPTION OF THE PREFERRED EMBODIMENTS

First Embodiment

Figure 1:
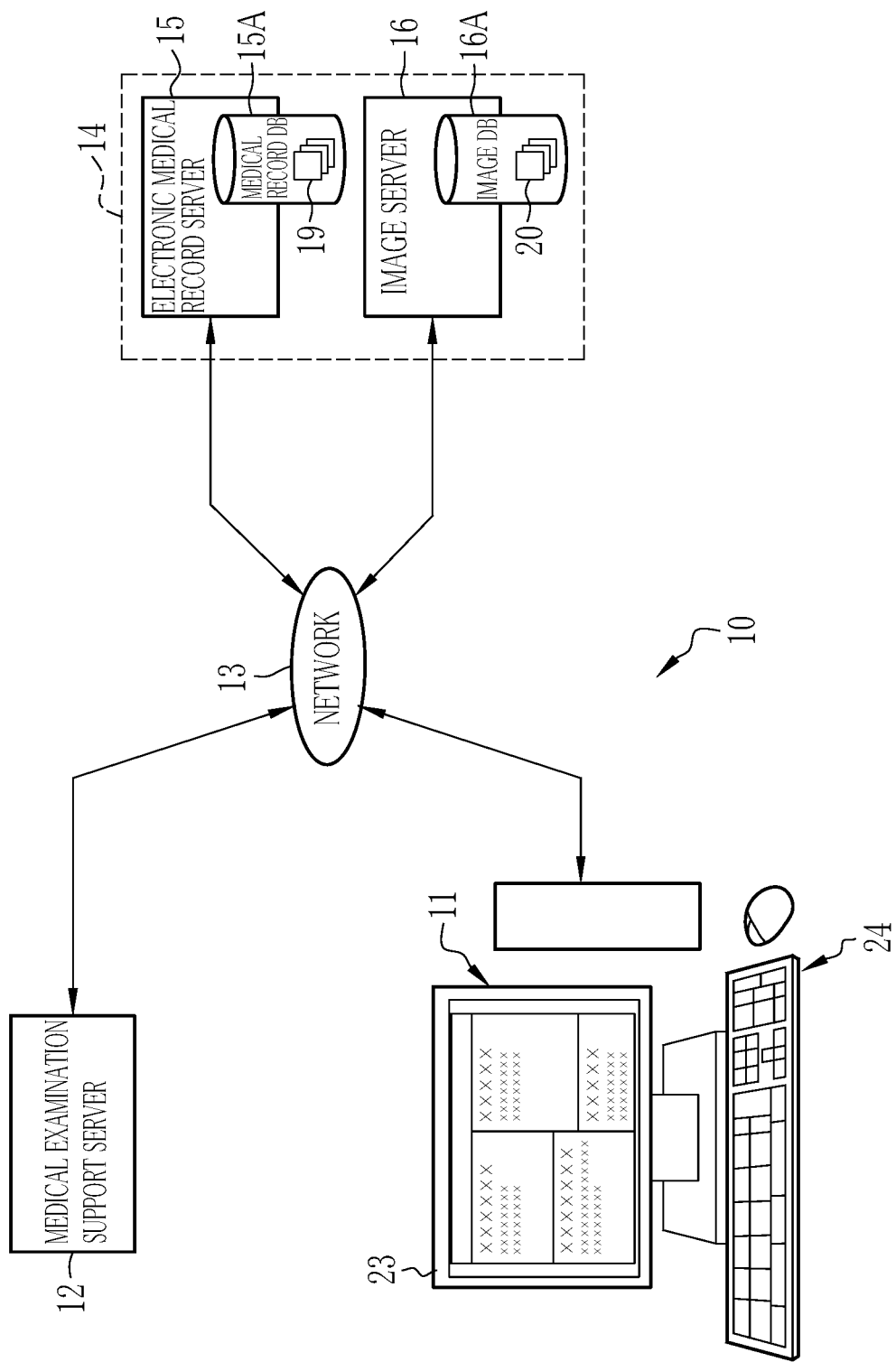
FIG. 1 is a diagram illustrating a medical examination system.

In FIG. 1, a medical examination system 10 is constructed in a medical facility, and includes a client terminal 11, a medical examination support server 12 corresponding to a medical examination support apparatus, and the like. The client terminal 11 and the medical examination support server 12 are connected to each other communicably through a network 13, such as a local area network (LAN) provided in the medical facility.

A server group 14 is also connected to the network 13. The server group 14 includes an electronic medical record server 15, and an image server 16. The electronic medical record server 15 has a medical record database (hereinafter, referred to as DB) 15A, and electronic medical records 19 are stored in the medical record DB 15A in a searchable manner. The image server 16 has an image DB 16A, and medical images 20 obtained by various image examinations are stored in the image DB 16A in a searchable manner.

The image examination is a kind of medical examination, and the medical image 20 is a kind of examination data. The image examination includes a computed radiography (CR) examination, a CT examination, an MRI examination, an electro cardiogram (ECG) examination, a coronary angiography (CAG) examination, an ultrasonography (US) examination, an endoscopic examination, and the like. The medical image 20 of the CR examination, the CT examination, the MRI examination, or the like is created in a data file format of a digital imaging and communications in medicine (DICOM) standard, for example.

The client terminal 11, the medical examination support server 12, and the server group 14 are configured by installing a control program such as an operating system and various application programs based on a computer such as a personal computer, a server computer, and a workstation.

The client terminal 11 includes a display 23 for displaying various display screens, and an input device 24 such as a keyboard and a mouse, and is operated by a medical staff. In FIG. 1, only one client terminal 11 is illustrated, but a plurality of client terminals 11 are provided in practice for each medical department, such as internal medicine, surgery, examination department, and rehabilitation department, or each medical staff. The client terminal 11 is used to perform a medical examination for a patient by using various functions of the medical examination support server 12 and the server group 14.

Since the medical examination support server 12 supports medical examination of the medical staff, particularly, the doctor, the medical examination support server 12 processes various kinds of medical data obtained during the medical examination for the patient and provides the results to the doctor. The medical data includes the examination data.

Figure 2:
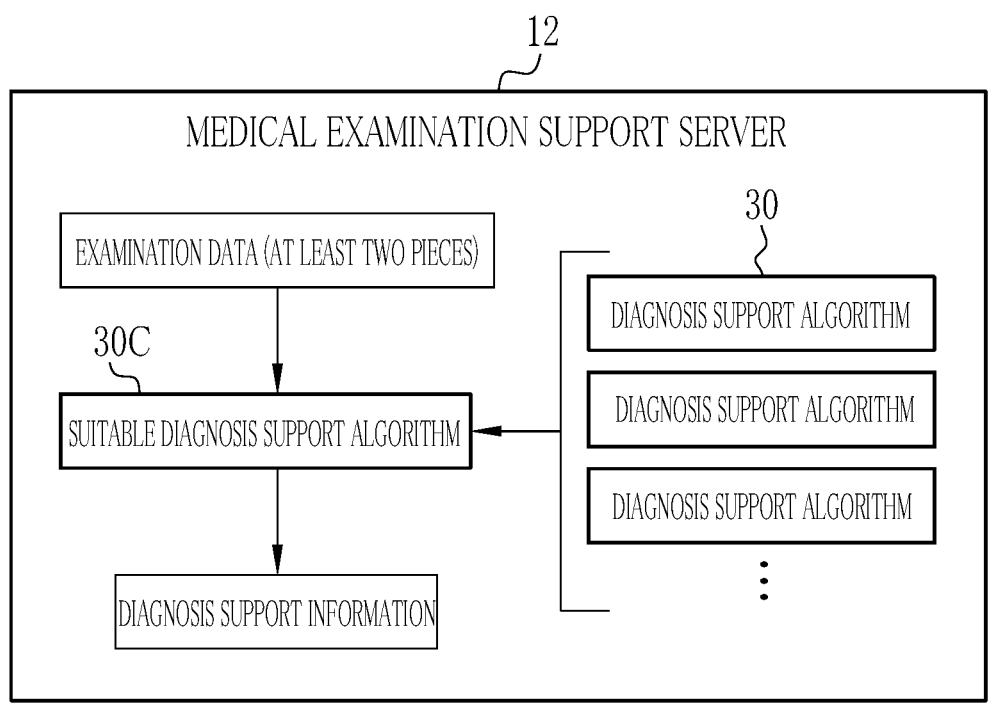
FIG. 2 is a diagram illustrating an outline of medical examination support using a diagnosis support algorithm.

As illustrated in FIG. 2, the medical examination support server 12 uses a diagnosis support algorithm 30 as a part of the medical examination support. More specifically, the medical examination support server 12 inputs the examination data to the diagnosis support algorithm 30 and causes the diagnosis support algorithm 30 to automatically perform analysis processing on the examination data and output the result of the analysis processing as diagnosis support information for supporting the diagnosis of the doctor.

At least two pieces of examination data are input to the diagnosis support algorithm 30. The details of the at least two pieces of examination data may be the same type or different types, and for example, may be two CT images or a US image and an endoscopic image. For at least two pieces of examination data, selection instructions are made in the client terminal 11.

There are a plurality of diagnosis support algorithms 30. In the medical examination support server 12, from among the plurality of diagnosis support algorithms 30, a suitable diagnosis support algorithm 30C according to the at least two pieces of examination data is selected. Therefore, the diagnosis support information is output by performing analysis processing in the suitable diagnosis support algorithm 30C.

Figure 3:
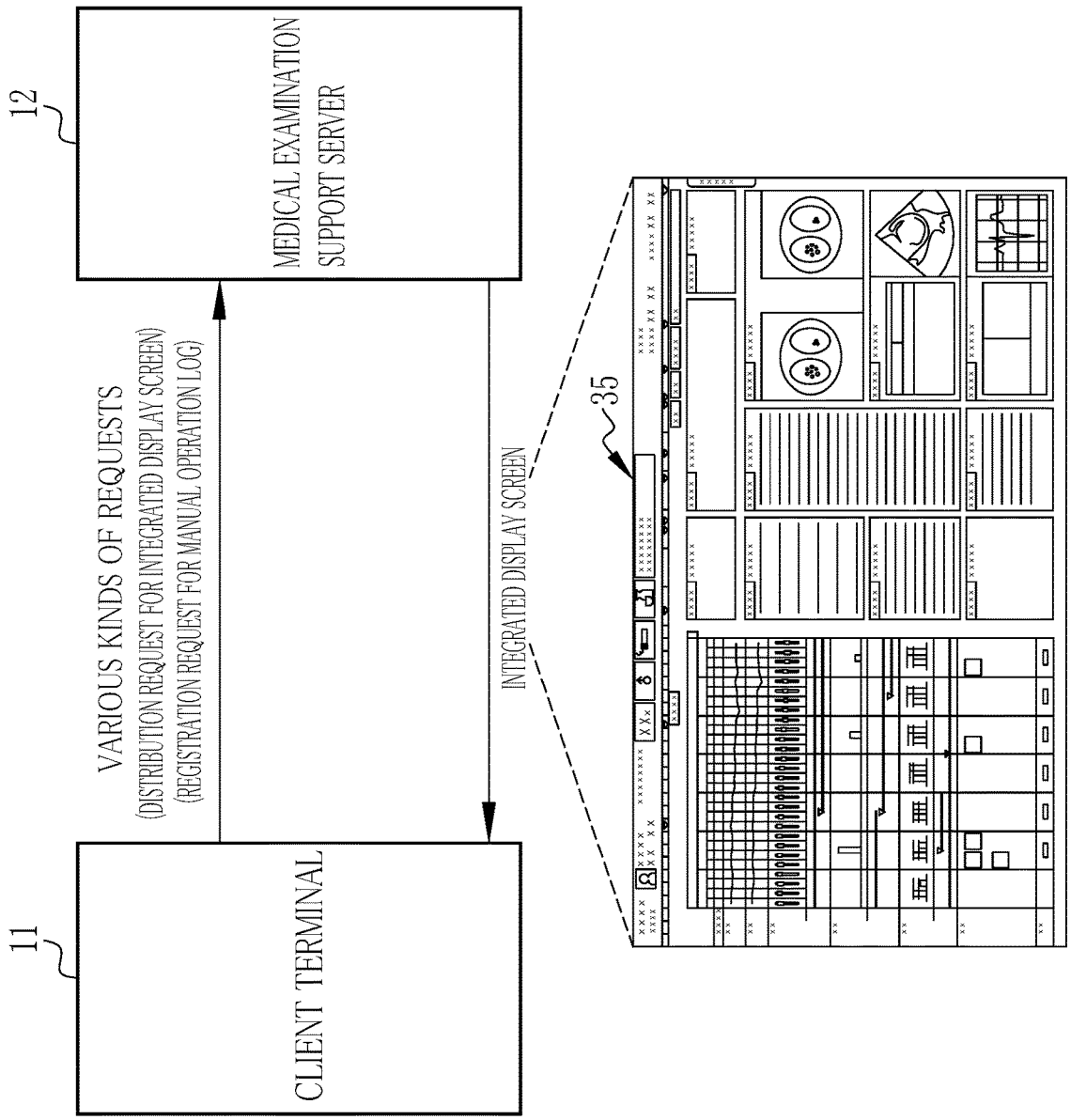
FIG. 3 is a diagram illustrating various kinds of information transmitted and received between a client terminal and a medical examination support server.

In FIG. 3, the medical examination support server 12 receives various requests from the client terminal 11. The various requests include a distribution request for an integrated display screen 35 (refer to also FIG. 11), an editing request for various display screens, and the like.

The integrated display screen 35 is a display screen in which various kinds of medical data of a patient to be treated (hereinafter, referred to as target patient) are combined into one for the doctor to easily perform analysis. The medical examination support server 12 acquires various kinds of medical data of the target patient according to the distribution request for the integrated display screen 35, from the server group 14, and generates the integrated display screen 35 on the basis of the acquired various kinds of medical data. The medical examination support server 12 transmits the generated integrated display screen 35 to the client terminal 11 that is a request source of the distribution request. The client terminal 11 outputs the integrated display screen 35 from the medical examination support server 12 to the display 23.

The medical examination support server 12 generates the integrated display screen 35 that can be viewed on a web browser, and transmits the integrated display screen 35 to the client terminal 11. The medical examination support server 12 issues an authentication key to the client terminal 11 to give a right for accessing the medical examination support server 12. After the client terminal 11 accesses the medical examination support server 12 and performs authentication, the integrated display screen 35 is transmitted from the medical examination support server 12 to the client terminal 11, and is displayed on the display 23.

The medical examination support server 12 outputs various display screens including the integrated display screen 35 in a format of web distribution screen data created in a markup language such as Extensible Markup Language (XML), for example. The client terminal 11 reproduces and displays various display screens on the web browser on the basis of the screen data. Instead of the XML, other data description languages, such as JavaScript (registered trademark) Object Notation (JSON), may be used.

Figure 4:
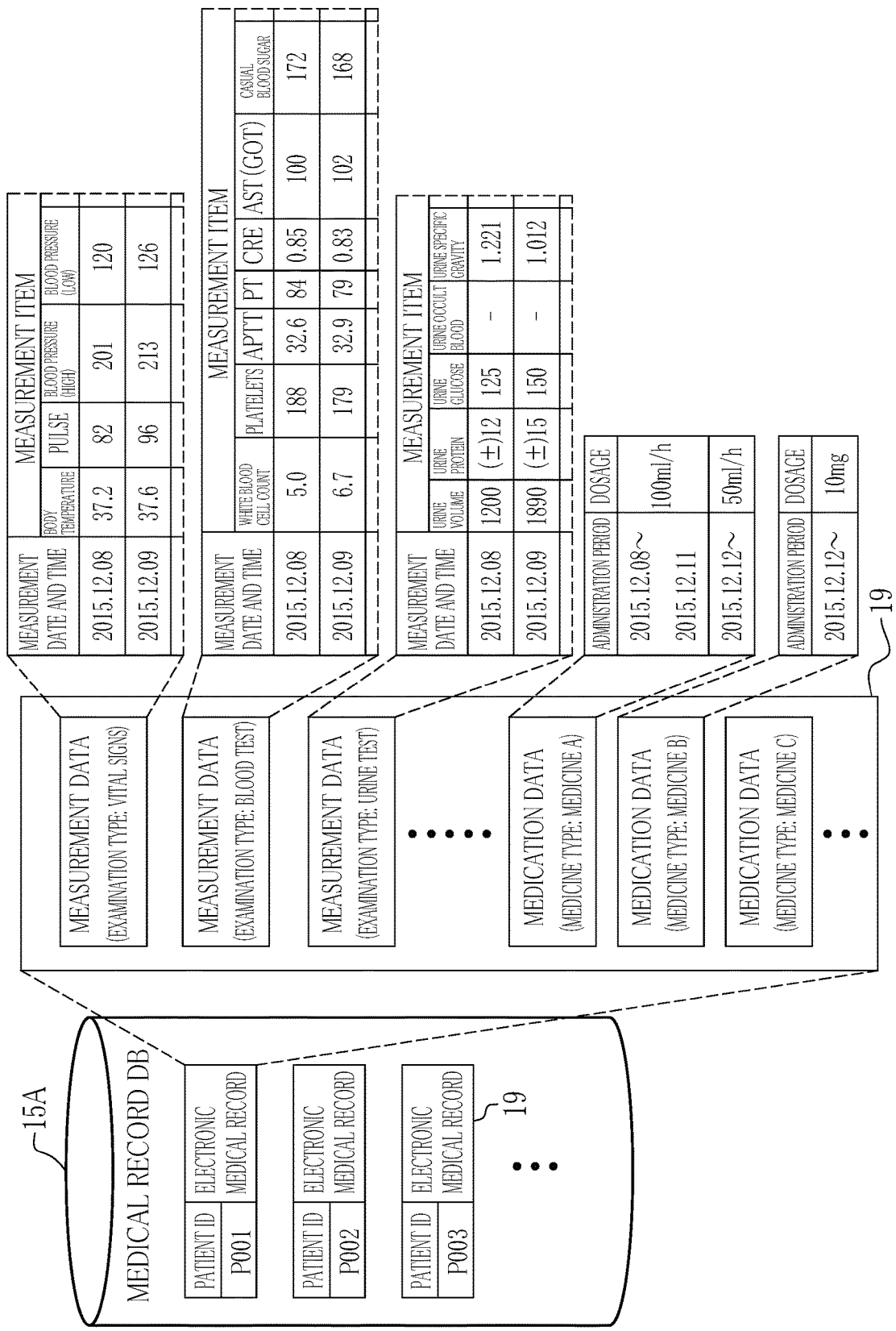
FIG. 4 is a diagram illustrating contents of electronic medical records stored in a medical record DB.

In FIG. 4, the electronic medical record 19 of the medical record DB 15A is managed for each patient in association with a patient identification data (ID) which is a symbol and a number for identifying each patient such as P001. The electronic medical record server 15 can search for the electronic medical record 19 from the medical record DB 15A using the patient ID as a search key.

The electronic medical record 19 has a plurality of pieces of measurement data and a plurality of pieces of medication data, as medical data. The measurement data is a kind of examination data as in case of the medical image 20. The measurement data is organized by type of medical examination such as vital signs, blood tests, or urine tests, and is stored in association with the measurement date and time, measurement items, and measurement values. The measurement items include, for example, in case of vital signs, the body temperature, pulse, blood pressure (high and low), and the like, and include, in case of a blood test, the white blood cell count, platelets, casual blood sugar, and the like. The medication data is organized by type of medicines such as a medicine A and a medicine B, and is stored in association with an administration period and a dosage.

In the electronic medical record 19, in addition to the patient ID, patient information such as the name, gender, age, date of birth, preference (smoking, drinking), past illness, and allergies of the patient is recorded. Further, in the electronic medical record 19, medical examination, creation of the medical report, orders with instructions of surgery, medication, and the like, events that occurred during the medical examination for the patient such as initial consultation, re-examination, and hospitalization, or a consultation record including patient's chief complaint and diagnosis name, a nursing record, and information from the patient's family are also recorded in time series.

Figure 5:
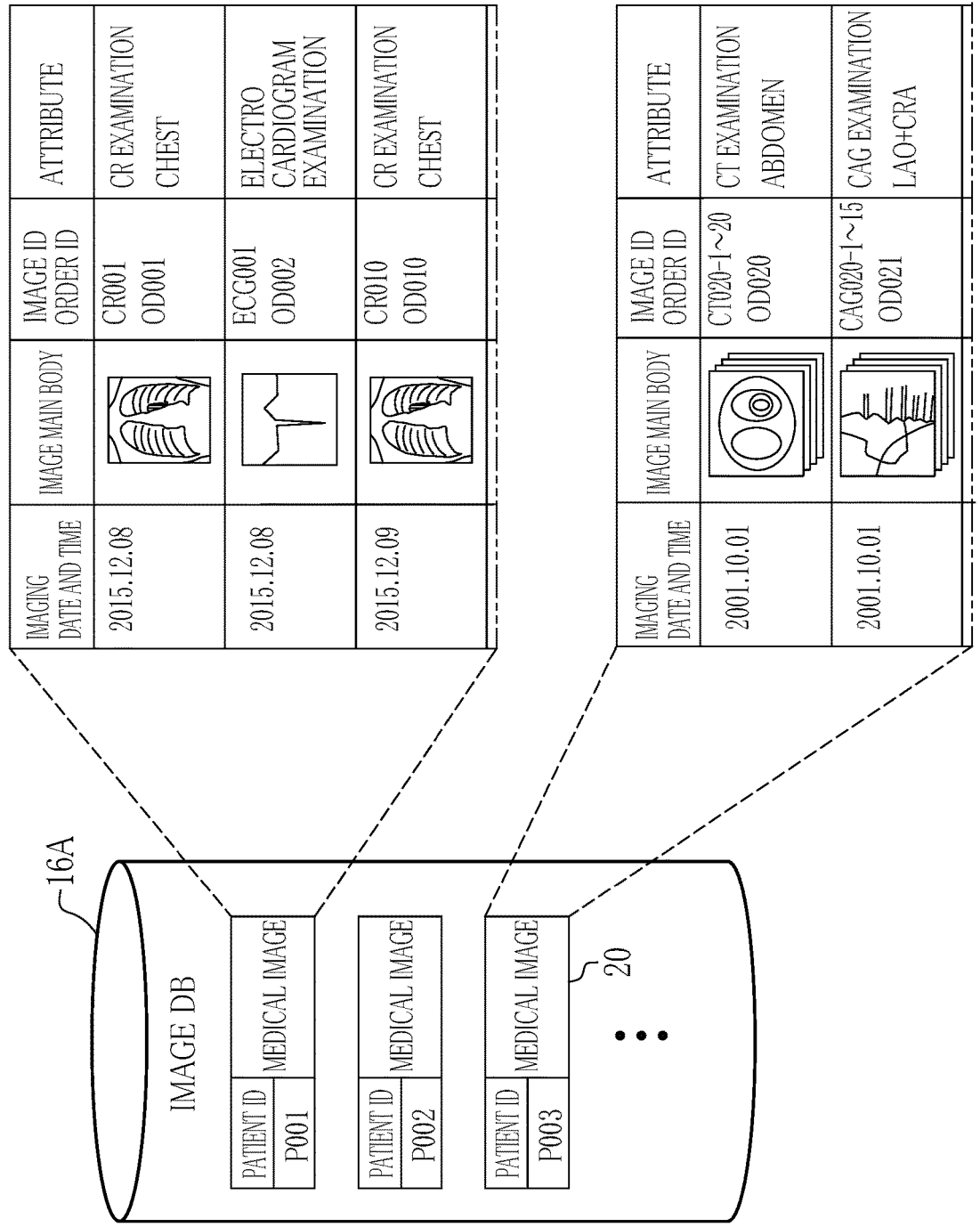
FIG. 5 is a diagram illustrating contents of medical images stored in an image DB.

In FIG. 5, the medical image 20 of the image DB 16A is managed for each patient in association with the patient ID as in case of the electronic medical record 19. As in case of the electronic medical record server 15, the image server 16 can search for the medical image 20 from the image DB 16A using the patient ID as a search key.

A file of the medical images 20 for one case includes the main body of the medical image 20, and various kinds of additional information such as imaging date and time, an image ID, an order ID, and attributes (type of image examination, imaging part, direction). The image server 16 transmits the medical image 20 together with the additional information as the medical data to the medical examination support server 12.

The image ID is a symbol and a number for identifying each medical image 20, and the order ID is a symbol and a number for identifying an order of instructing various kinds of image examinations. In case of an image examination in which a plurality of medical images 20 are captured at one time, such as CT examination or CAG examination, in order to indicate that a plurality of medical images 20 are obtained at one image examination, the medical images 20 are assigned a common order ID, and are collectively managed as the medical image 20.

Figure 6:
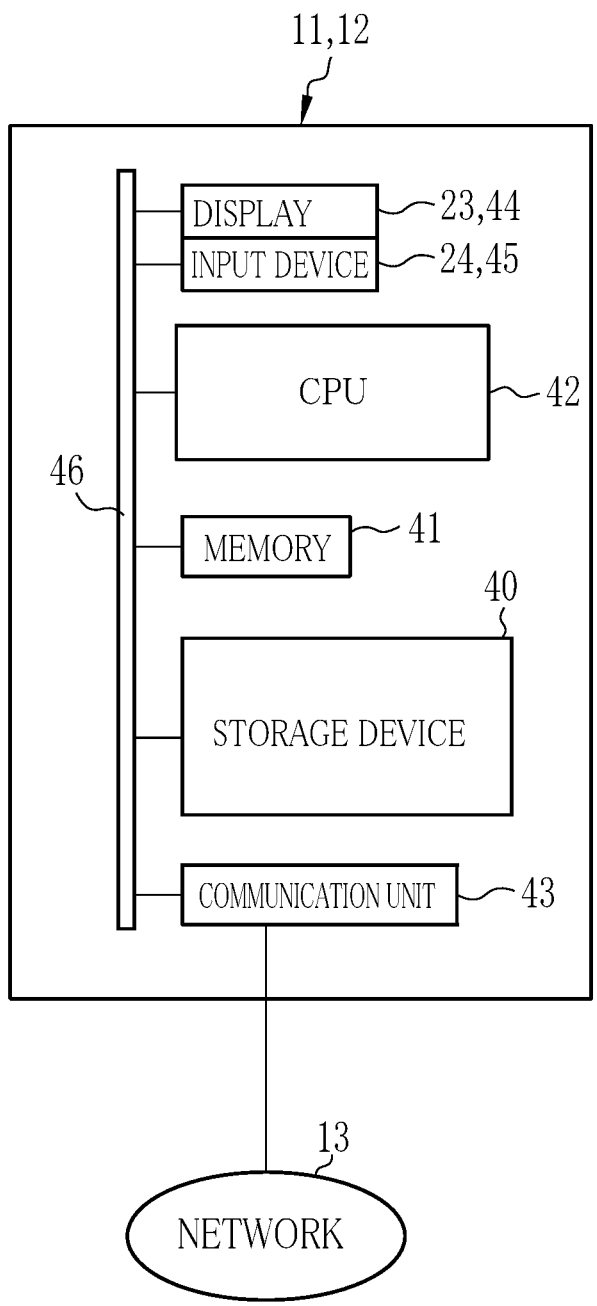
FIG. 6 is a block diagram illustrating a computer constituting the client terminal and the medical examination support server.

In FIG. 6, the computers constituting the client terminal 11 and the medical examination support server 12 have basically the same configuration, and each of the computers includes a storage device 40, a memory 41, a central processing unit (CPU) 42, and a communication unit 43. The client terminal 11 includes the display 23 and the input device 24 as described above, and similarly, the medical examination support server 12 includes a display 44 and an input device 45. These are connected to each other through a data bus 46.

The storage device 40 is a hard disk drive, which is built into a computer that constitutes the client terminal 11 or the like or which is connected to the computer through a cable or a network, or a disk array formed by connecting a plurality of hard disk drives. Control programs such as an operating system, various application programs, and display data of various display screens associated with these programs are stored in the storage device 40.

The memory 41 is a work memory required for the CPU 42 to execute processing. The CPU 42 performs overall control of each unit of the computer by loading a program stored in the storage device 40 to the memory 41 and executing processing according to the program.

The communication unit 43 is a network interface to perform transmission control of various kinds of information through the network 13. The displays 23 and 44 display various display screens according to the operations of the input devices 24 and 45. The display screen has an operation function based on the graphical user interface (GUI). The computer constituting the client terminal 11 or the like receives an input of an operation instruction from the input devices 24 and 45 through the display screen.

In the following description, for the sake of distinction, a suffix "A" is attached to the reference numeral of each unit of the computer constituting the client terminal 11 except for the display 23 and the input device 24, and a suffix "B" is attached to the reference numeral of each unit of the computer constituting the medical examination support server 12 except for the display 44 and the input device 45.

Figure 7:
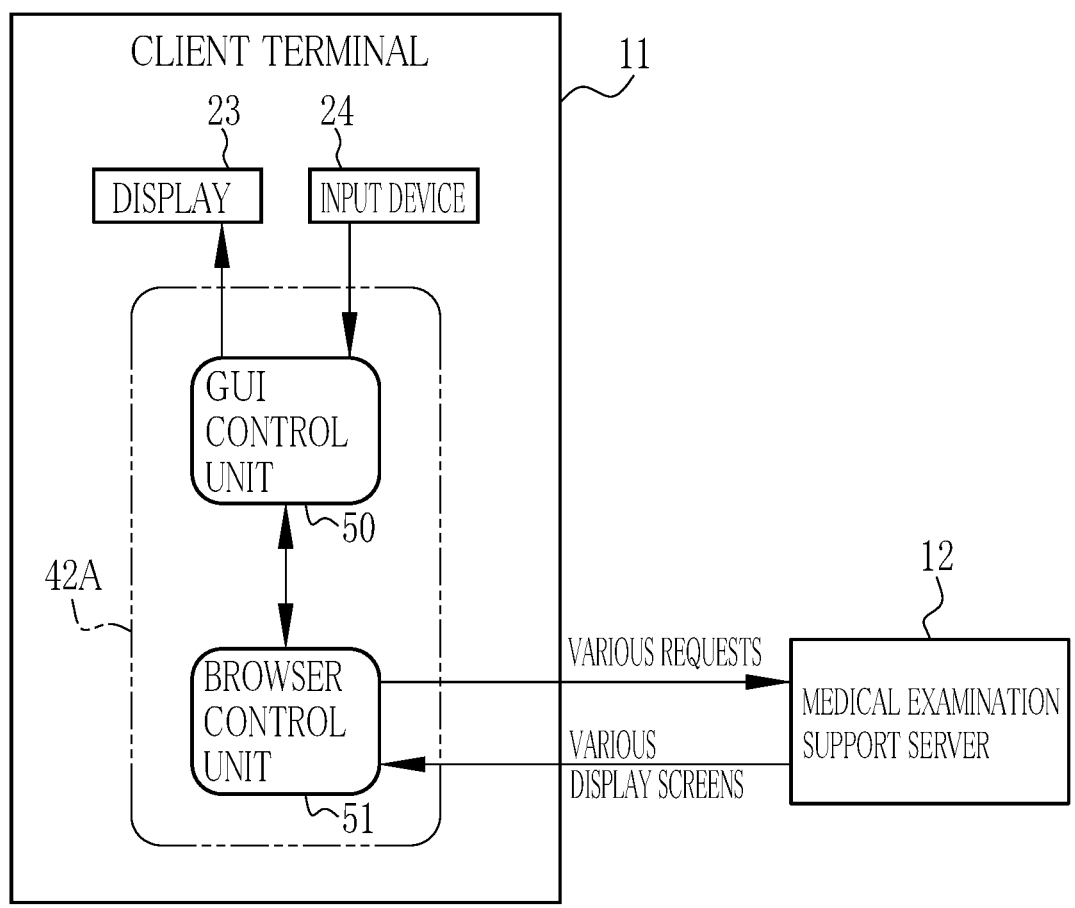
FIG. 7 is a block diagram illustrating various processing units of a CPU of the client terminal.

In FIG. 7, in a case where a web browser is started, the CPU 42A of the client terminal 11 cooperates with the memory 41 or the like to function as a GUI control unit 50 and a browser control unit 51.

The GUI control unit 50 displays various display screens on the display 23, and receives various operation instructions which are input from the input device 24 through various display screens by the medical staff. The operation instructions include a distribution instruction of the integrated display screen 35 to the medical examination support server 12, an editing instruction of various display screens, and the like. The editing instruction of various display screens includes selection instructions of at least two pieces of examination data. The GUI control unit 50 outputs the received operation instruction to the browser control unit 51.

The browser control unit 51 controls the operation of the web browser. The browser control unit 51 issues a request according to the operation instruction from the GUI control unit 50, specifically a distribution request for the integrated display screen 35 according to the distribution instruction of the integrated display screen 35, an editing request for various display screens according to the editing instruction of various display screens, and the like, to the medical examination support server 12.

The browser control unit 51 receives screen data of each of various display screens from the medical examination support server 12. The browser control unit 51 reproduces the display screen to be displayed on the web browser based on the screen data, and outputs the display screen to the GUI control unit 50. The GUI control unit 50 displays the display screen on the display 23.

In FIG. 8, the storage device 40B of the medical examination support server 12 stores an operation program 55 in addition to the diagnosis support algorithm 30. The operation program 55 is an application program for causing a computer constituting the medical examination support server 12 to function as a medical examination support apparatus.

An algorithm correspondence table 56 (refer to FIG. 9) is also stored in the storage device 40B. In the algorithm correspondence table 56, at least two pieces of examination data and the suitable diagnosis support algorithm 30C are associated and stored.

In a case where the operation program 55 is activated, the CPU 42B of the medical examination support server 12 functions as a request receiving unit 60, a medical data acquisition unit 61, an algorithm selection unit 62, an analysis processing unit 63, an information management unit 64, and a screen output control unit 65, in cooperation with the memory 41 or the like.

The request receiving unit 60 receives various requests from the client terminal 11. The request receiving unit 60 outputs the distribution request for the integrated display screen 35 to the medical data acquisition unit 61, and the information management unit 65, and outputs the editing request for various display screens to the medical data acquisition unit 61, the algorithm selection unit 62, and the screen output control unit 65, among the various requests.

The editing instruction of various display screens as a trigger of the editing request for various display screens includes the selection instructions of at least two pieces of examination data as described above, and the editing request for various display screens in this case includes information of at least two pieces of examination data. Therefore, the request receiving unit 60 corresponds to an instruction receiving unit that receives selection instructions of at least two pieces of examination data among a plurality of pieces of examination data obtained in the medical examination performed on the patient, and has an instruction receiving function.

The medical data acquisition unit 61 issues an acquisition request for the medical data of the target patient to the server group 14. In the acquisition request, the patient ID of the target patient included in the distribution request for the integrated display screen 35 from the request receiving unit 60 is the search key. The medical data acquisition unit 61 acquires the medical data of the target patient transmitted from the server group 14 in response to the acquisition request. The medical data acquisition unit 61 outputs the acquired medical data to the screen output control unit 65. Further, the medical data acquisition unit 61 outputs, among the acquired medical data, the at least two pieces of examination data, of which the selection instructions are received, included in the editing request for various display screens to the analysis processing unit 63.

The algorithm selection unit 62 has an algorithm selection function of selecting the suitable diagnosis support algorithm 30C according to the at least two pieces of examination data of which the selection instructions are received by the request receiving unit 60, from among the plurality of diagnosis support algorithms 30. The algorithm selection unit 62 receives the algorithm correspondence table 56 from the information management unit 64, and performs selection by referring to the algorithm correspondence table 56. The algorithm selection unit 62 outputs the selection result to the analysis processing unit 63.

The analysis processing unit 63 has an analysis processing function of executing analysis processing by the suitable diagnosis support algorithm 30C. More specifically, the analysis processing unit 63 receives the selection result from the algorithm selection unit 62, and instructs the information management unit 64 to transfer the suitable diagnosis support algorithm 30C. Then, the at least two pieces of examination data from the medical data acquisition unit 61 are input to the suitable diagnosis support algorithm 30C which is transferred from the information management unit 64 according to the instruction. The analysis processing unit 63 outputs the diagnosis support information of the suitable diagnosis support algorithm 30C obtained in this manner, to the screen output control unit 65.

The information management unit 64 has an information management function of writing various kinds of information to the storage device 40B and reading various kinds of information from the storage device 40B. The information management unit 64 writes a new diagnosis support algorithm 30 to the storage device 40B according to an installation instruction of the new diagnosis support algorithm 30 via the input device 45. On the other hand, the information management unit 64 deletes the diagnosis support algorithm 30 from the storage device 40B according to an uninstallation instruction of the diagnosis support algorithm 30. The information management unit 64 updates the contents of the algorithm correspondence table 56 with installation and uninstallation of the diagnosis support algorithm 30.

The information management unit 64 outputs the algorithm correspondence table 56 to the algorithm selection unit 62 for reference at the time of selecting the suitable diagnosis support algorithm 30C. Further, the information management unit 64 outputs the suitable diagnosis support algorithm 30C of which the transfer is instructed, to the analysis processing unit 63.

The screen output control unit 65 generates the integrated display screen 35 on the basis of the medical data of the target patient from the medical data acquisition unit 61, and transmits the integrated display screen 35 to the client terminal 11 which is a request source of the distribution request for the integrated display screen 35. Further, the screen output control unit 65 generates an information display screen 95 (refer to FIG. 16) in which the diagnosis support information of the suitable diagnosis support algorithm 30C is displayed, and transmits the information display screen 95 to the client terminal 11 which is a request source of the distribution request for the integrated display screen 35. That is, the screen output control unit 65 has a screen output control function of controlling the output of the information display screen 95. Further, since the information display screen 95 is also transmitted in response to the distribution request for the integrated display screen 35, the distribution request for the integrated display screen 35 is a distribution request for the information display screen 95.

In FIG. 9, in the algorithm correspondence table 56, an algorithm ID of a suitable diagnosis support algorithm 30C according to at least two pieces of examination data is registered for the at least two pieces of examination data. The algorithm ID is a symbol and a number for identifying each diagnosis support algorithm 30. For example, in a case where the examination data is "two or more CT images having different imaging date and time", an algorithm ID "AL001" of a diagnosis support algorithm 30 of which the outline is lesion size change graph creation is registered.

In addition, in a case where the examination data is "two or more head CT images", two algorithm IDs, an algorithm ID "AL002" (diagnosis support algorithm 30 of which the outline is determination of morbidity risk of cerebral infarction) and an algorithm ID "AL003" (diagnosis support algorithm 30 of which the outline is determination of morbidity risk of dementia) are registered. In this manner, for the same set of examination data, a plurality of diagnosis support algorithms 30 are registered in some cases. The outline is provided for description, but is not registered in the actual algorithm correspondence table 56.

Figure 10:
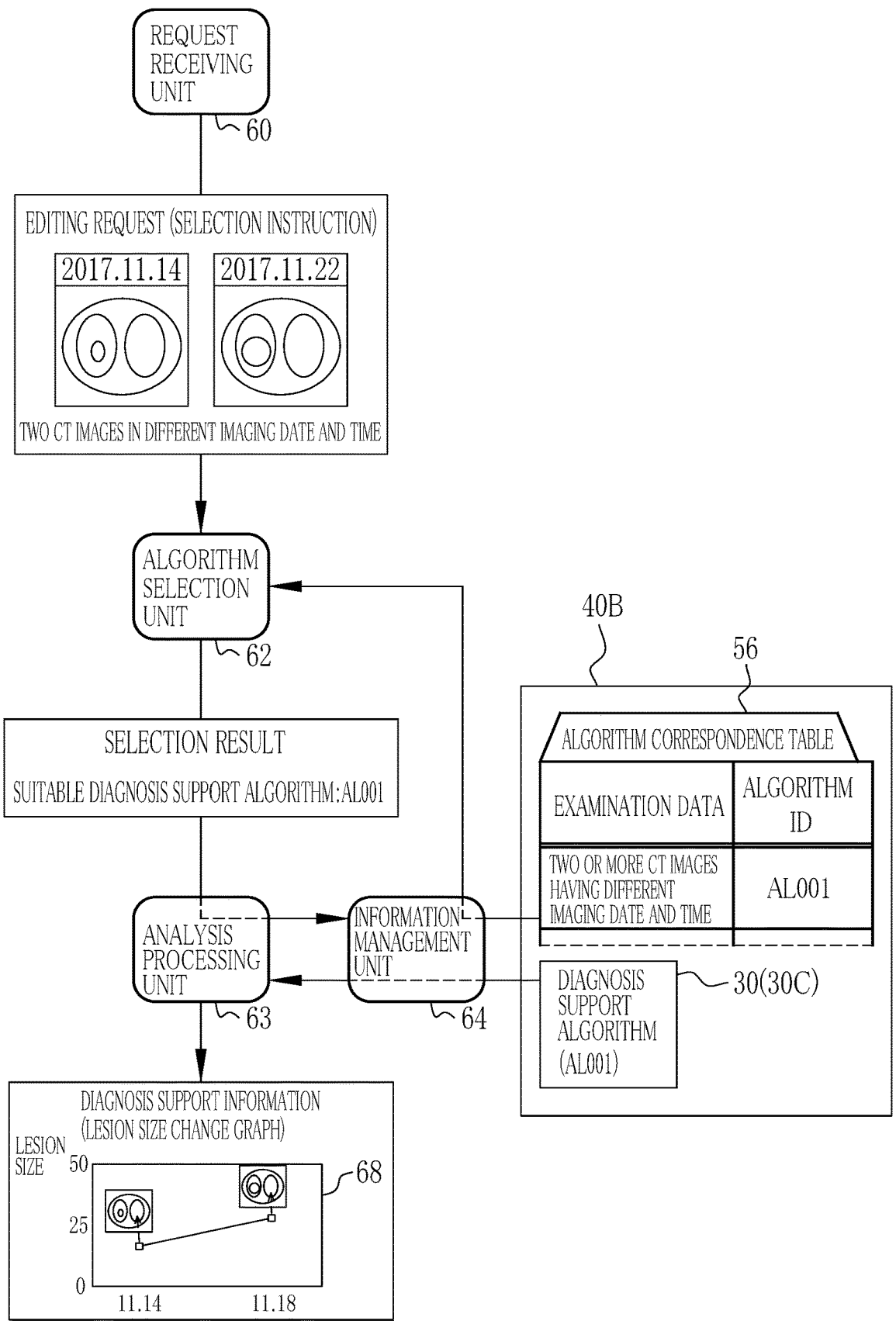
FIG. 10 is a diagram illustrating a flow of processing of receiving selection instructions of at least two pieces of examination data, selecting a suitable diagnosis support algorithm according to the selection instruction, and outputting diagnosis support information of the suitable diagnosis support algorithm.

FIG. 10 illustrates a case in which the at least two pieces of examination data of which the selection instructions are received by the request receiving unit 60 are two CT images having different imaging date and time. In this case, the algorithm selection unit 62 refers to the algorithm correspondence table 56 from the information management unit 64, and extracts the algorithm ID "AL001" of a case where the examination data is "two or more CT images having different imaging date and time". The algorithm selection unit 62 outputs the extracted algorithm ID "AL001" to the analysis processing unit 63 as the selection result.

The analysis processing unit 63 instructs the information management unit 64 to transfer the diagnosis support algorithm 30 having the algorithm ID "AL001" which is the selection result from the algorithm selection unit 62. The information management unit 64 transfers the diagnosis support algorithm 30 having the algorithm ID "AL001" of which the transfer is instructed, to the analysis processing unit 63. The diagnosis support algorithm 30 having the algorithm ID "AL001" is the suitable diagnosis support algorithm 30C in this case.

The analysis processing unit 63 inputs two CT images having different imaging date and time to the diagnosis support algorithm 30 having the algorithm ID "AL001" transferred from the information management unit 64. As a result, diagnosis support information is output. Since the diagnosis support algorithm 30 having the algorithm ID "AL001" is for creating a lesion size change graph as described above, a lesion size change graph 68 is output as the diagnosis support information.

The medical staff accesses the medical examination support server 12 via the client terminal 11, and performs authentication by inputting his/her own staff ID and an authentication key. After authentication, an input screen for the patient ID is displayed on the web browser of the display 23 of the client terminal 11. In the input screen for the patient ID, for example, an input box for the patient ID, and a transmission button for performing a distribution instruction of the integrated display screen 35 are prepared. In a case where a patient ID of the target patient is input to the input box and the transmission button is selected, a distribution request for the integrated display screen 35 including a patient ID of the target patient is issued from the browser control unit 51 of the client terminal 11 to the request receiving unit 60 of the medical examination support server 12.

The distribution request for the integrated display screen 35 is received, and the acquisition request is issued from the medical data acquisition unit 61 to the server group 14. The server group 14 transmits the medical data such as the electronic medical record 19 and the medical image 20 to which the patient ID of the target patient is assigned, to the medical data acquisition unit 61. The screen output control unit 65 generates the integrated display screen 35 illustrated in FIG. 11 on the basis of the medical data of the target patient from the server group 14.

Figure 11:
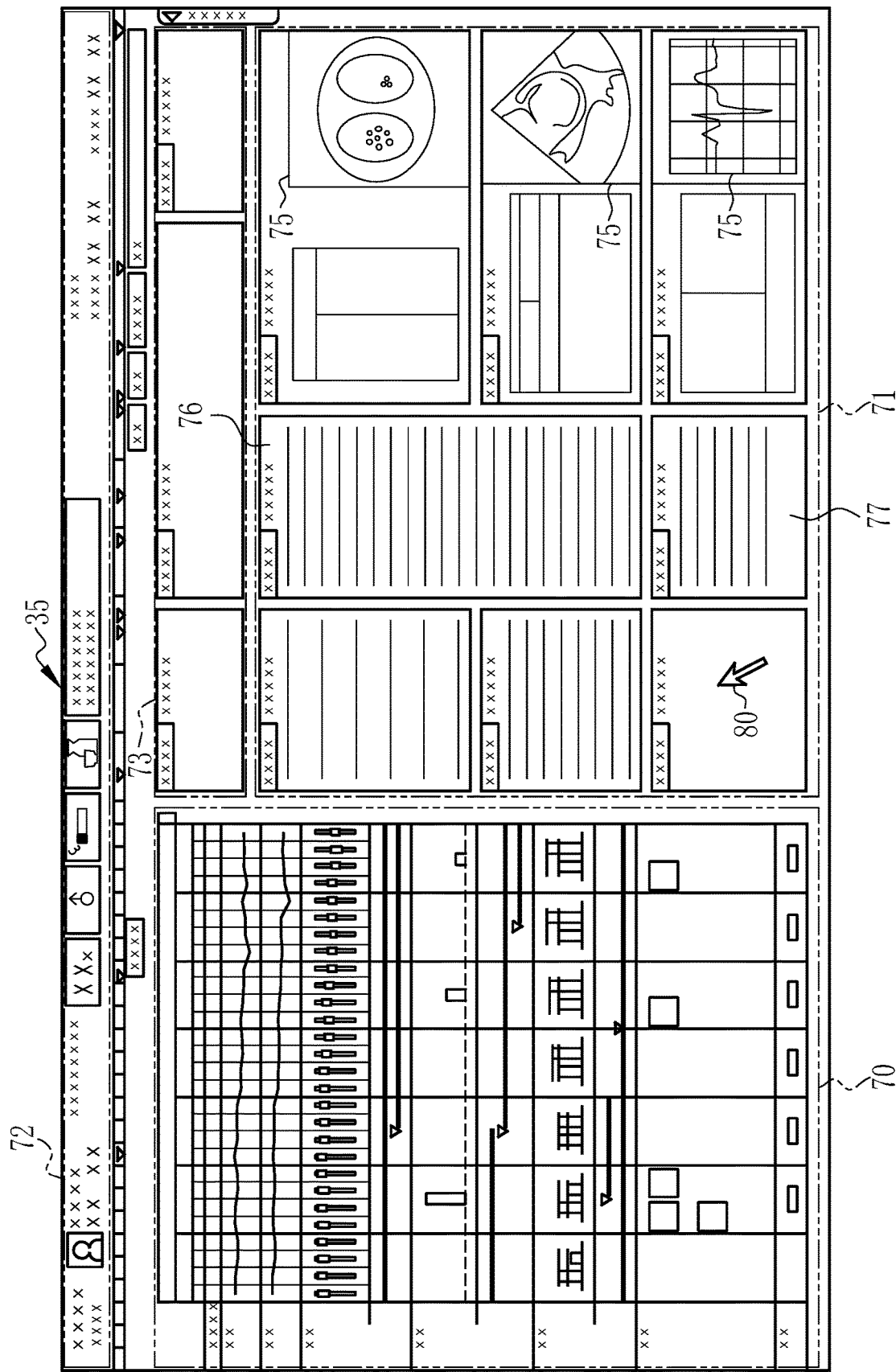
FIG. 11 is a diagram illustrating an integrated display screen.

In FIG. 11, the integrated display screen 35 is divided into roughly four display regions of a first display region 70, a second display region 71, a third display region 72, and a fourth display region 73. In the first display region 70, a graph indicating a time-series change of a measurement value of each measurement item such as the body temperature, pulse, and blood pressure (high and low) of vital signs, a bar indicating a dosage and an administration period of the medicine, and the like are displayed.

In the second display region 71, a plurality of windows displaying the medical data are displayed side by side. For example, measurement values of representative measurement items among a plurality of measurement items of the blood test are displayed in a list in a certain window, and measurement values of representative measurement items among a plurality of measurement items of the urine test are displayed in a list in a certain window. Further, there is a window in which the type and the dosage of the medicine are displayed in a list. There are windows in which a thumbnail 75 of each of various medical images 20 is displayed, as three windows arranged on a right end of the second display region 71. The latest medical data is displayed in each window of the second display region 71.

In the third display region 72, patient information of the target patient, such as the patient ID, the name, gender, age, date of birth, preference, past illness, and allergies, and the affiliation medical department and the name of the attending physician of the target patient are displayed. In the fourth display region 73, windows displaying the patient's chief complaint, the consultation record, the nursing record, and the information from the patient's family included in the electronic medical record 19 are displayed side by side.

Each window in the second display region 71 can be selected by a cursor 80. The selection of each window in the second display region 71 is included in the editing instruction.

Figure 12:
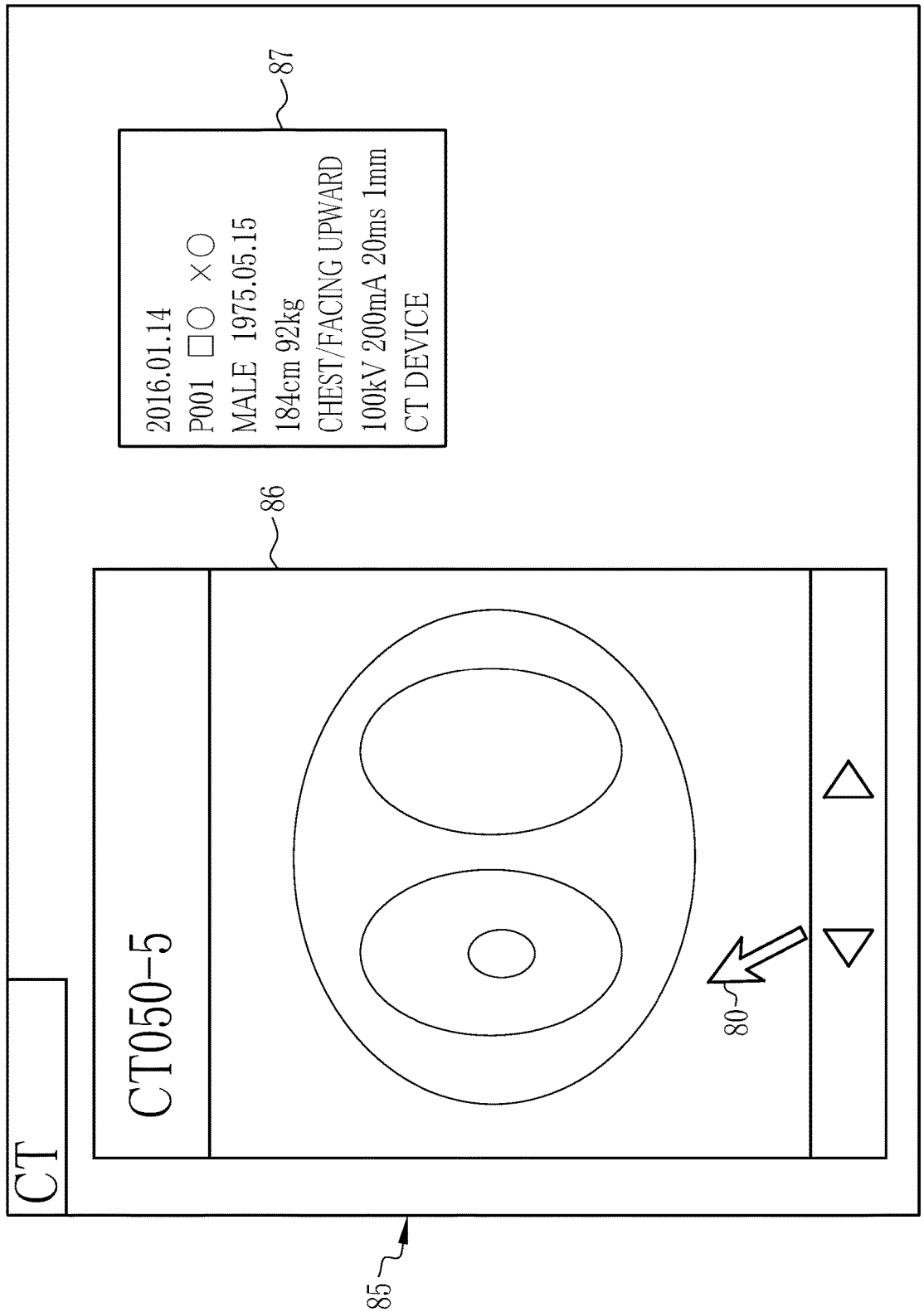
FIG. 12 is a diagram illustrating a viewer screen.

For example, in a case where a window in which the thumbnail 75 is displayed is selected by the cursor 80, the screen output control unit 65 causes a viewer screen 85 illustrated in FIG. 12 to be displayed in a pop-up on the integrated display screen 35.

In FIG. 12, the viewer screen 85 includes an image display region 86 in which a full-size medical image 20 is displayed, and an information display region 87 in which the patient information such as the patient ID and the additional information such as the patient's name, the imaging date and time, the imaging part, and the direction are displayed.

In the viewer screen 85, a full-size medical image 20 is displayed instead of the thumbnail 75 in the integrated display screen 35. Further, detailed information of the medical image 20 can be checked by the information display region 87. That is, the viewer screen 85 displays detailed information of the examination data.

In a case where a window in which measurement values of representative measurement items among a plurality of measurement items of the blood test or the urine test are displayed in a list is selected by the cursor 80, a screen in which all of the measurement values of the plurality of measurement items are displayed is displayed in a pop-up on the integrated display screen 35. The screen in which the measurement values of all of the measurement items are displayed also displays detailed information of the examination data, similar to the viewer screen 85.

Figure 13:
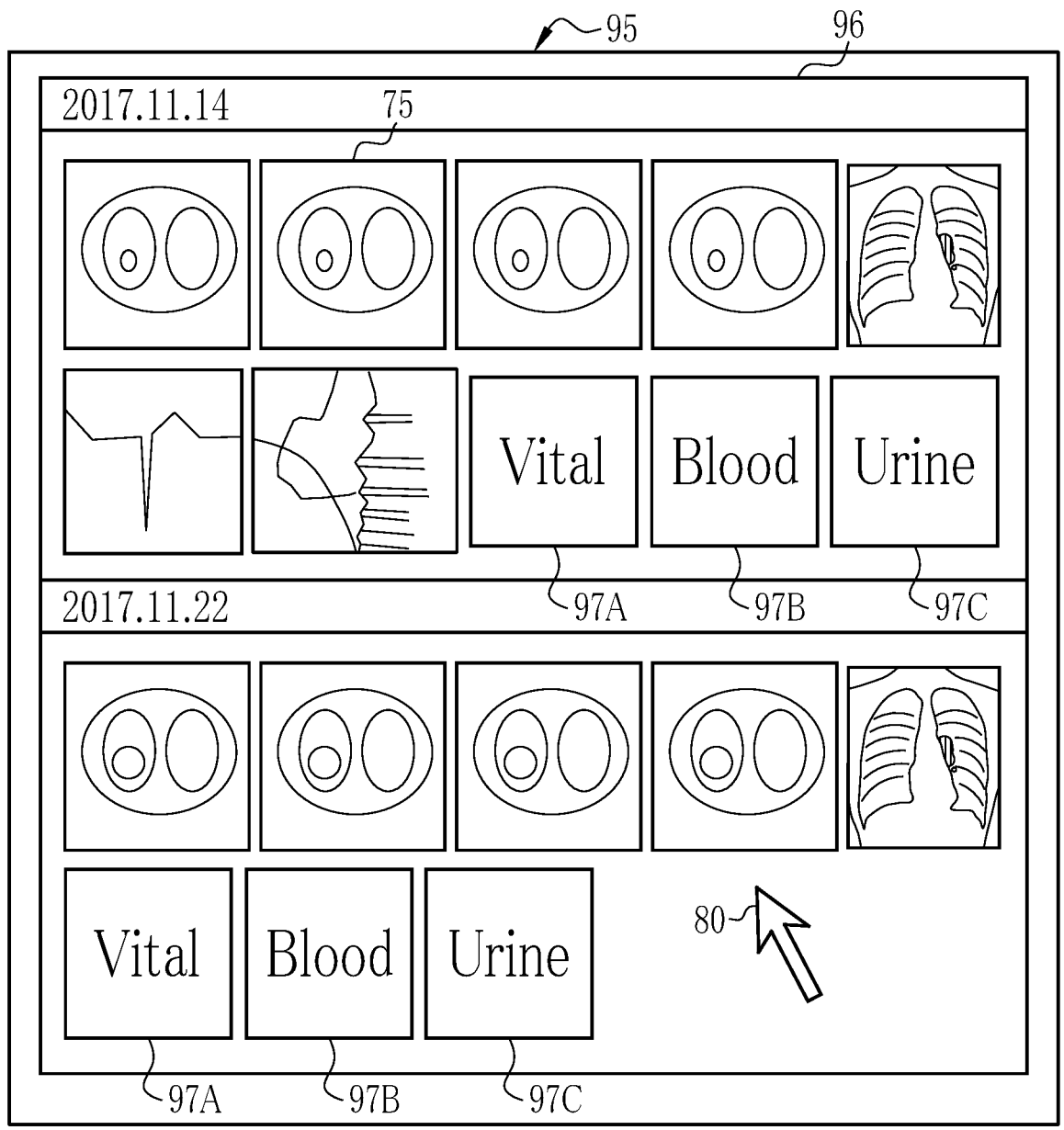
FIG. 13 is a diagram illustrating an information display screen in a state where examination data is not selected.

The screen output control unit 65 causes the information display screen 95 illustrated in FIG. 13 to be displayed on the side or the like of the integrated display screen 35.

In FIG. 13, the information display screen 95 has a list display region 96. The list display region 96 more simply indicates the display of each window in the second display region 71 of the integrated display screen 35, and is divided into small regions for each day. In each small region, icons indicating the results of the medical examinations performed on that day are displayed in a list. That is, the thumbnails 75 of various medical images 20 as the results of various image examinations, and icons 97A, 97B, and 97C respectively corresponding to the vital sign, the blood test, and the urine test are displayed.

In the list display region 96, a plurality of pieces of examination data are displayed in a list in order to receive the selection instruction. More specifically, in the list display region 96, similar to each window in the second display region 71, the thumbnails 75 and the icons 97A to 97C can be selected by the cursor 80.

Figure 14A:
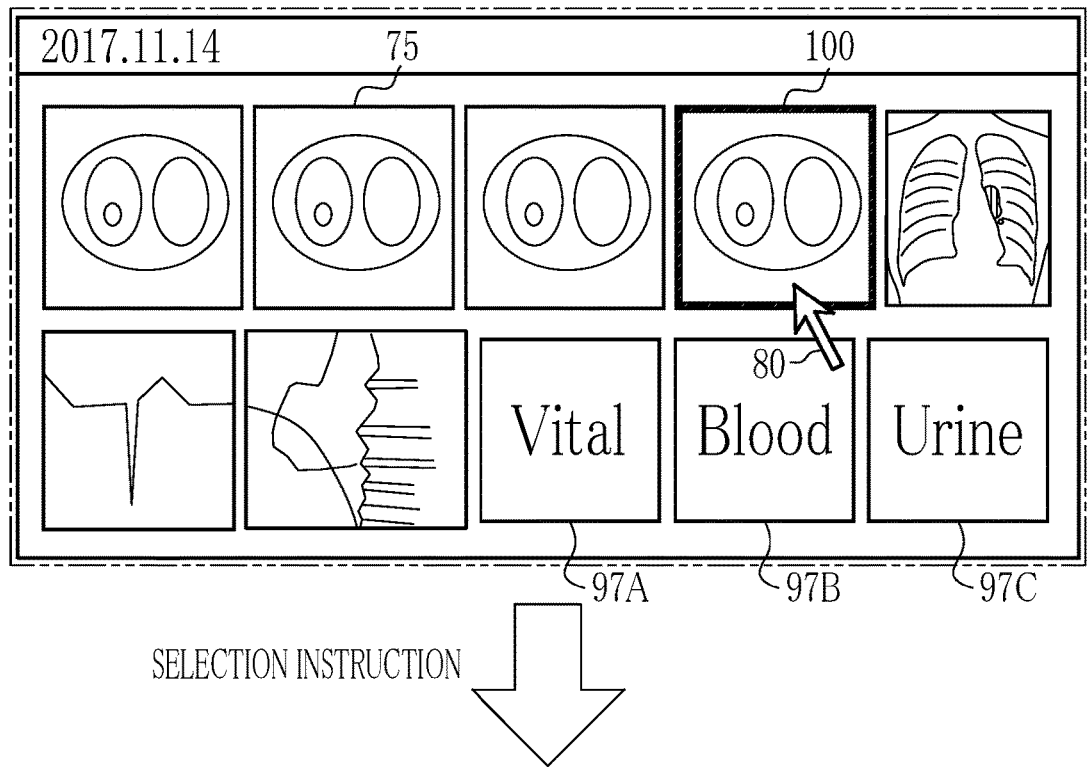
FIGS. 14A and 14B are diagrams illustrating an aspect in which detailed information of one piece of examination data of which a selection instruction is received is displayed.
Figure 14B:
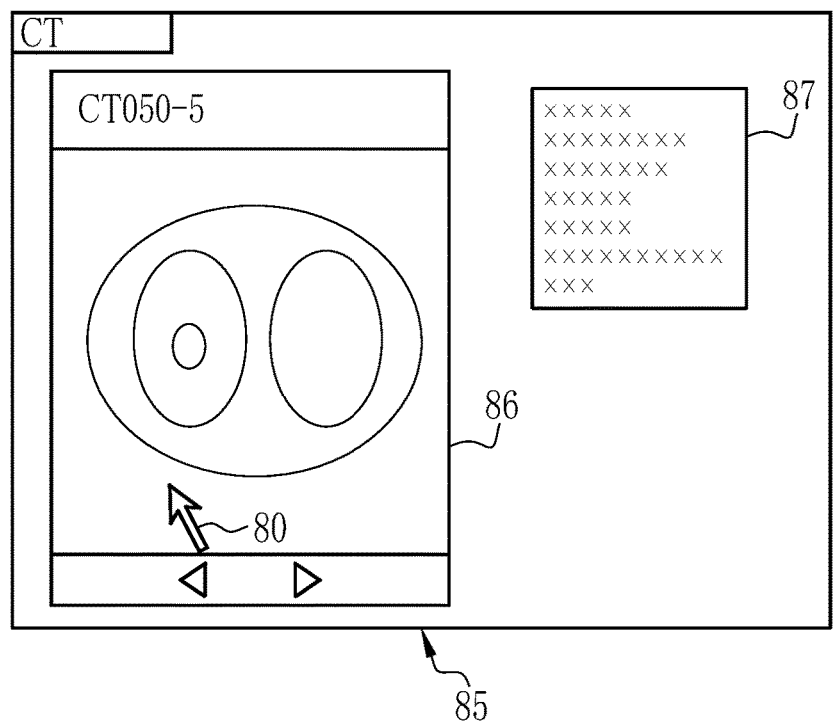

In a case where the thumbnail 75 is selected by the cursor 80 as illustrated in FIG. 14A, the screen output control unit 65 causes the viewer screen 85 illustrated in FIG. 12 to be displayed as illustrated in FIG. 14B. Further, although not illustrated, in a case where the icons 97A to 97C are selected by the cursor 80, the screen output control unit 65 causes a screen in which the measurement values of all of the measurement items of each examination are displayed to be displayed. The reference numeral 100 indicates a frame indicating that selection is made by the cursor 80.

The selection instruction of the thumbnails 75 and the icons 97A to 97C corresponds to the selection instruction of one piece of examination data. Further, the viewer screen 85 and the screen in which the measurement values of all of the measurement items are displayed display detailed information of the examination data as described above. That is, in a case where the selection instruction of one piece of examination data is received by the request receiving unit 60, the screen output control unit 65 displays detailed information of the one piece of examination data of which the selection instruction is received by the request receiving unit 60.

Figure 15:
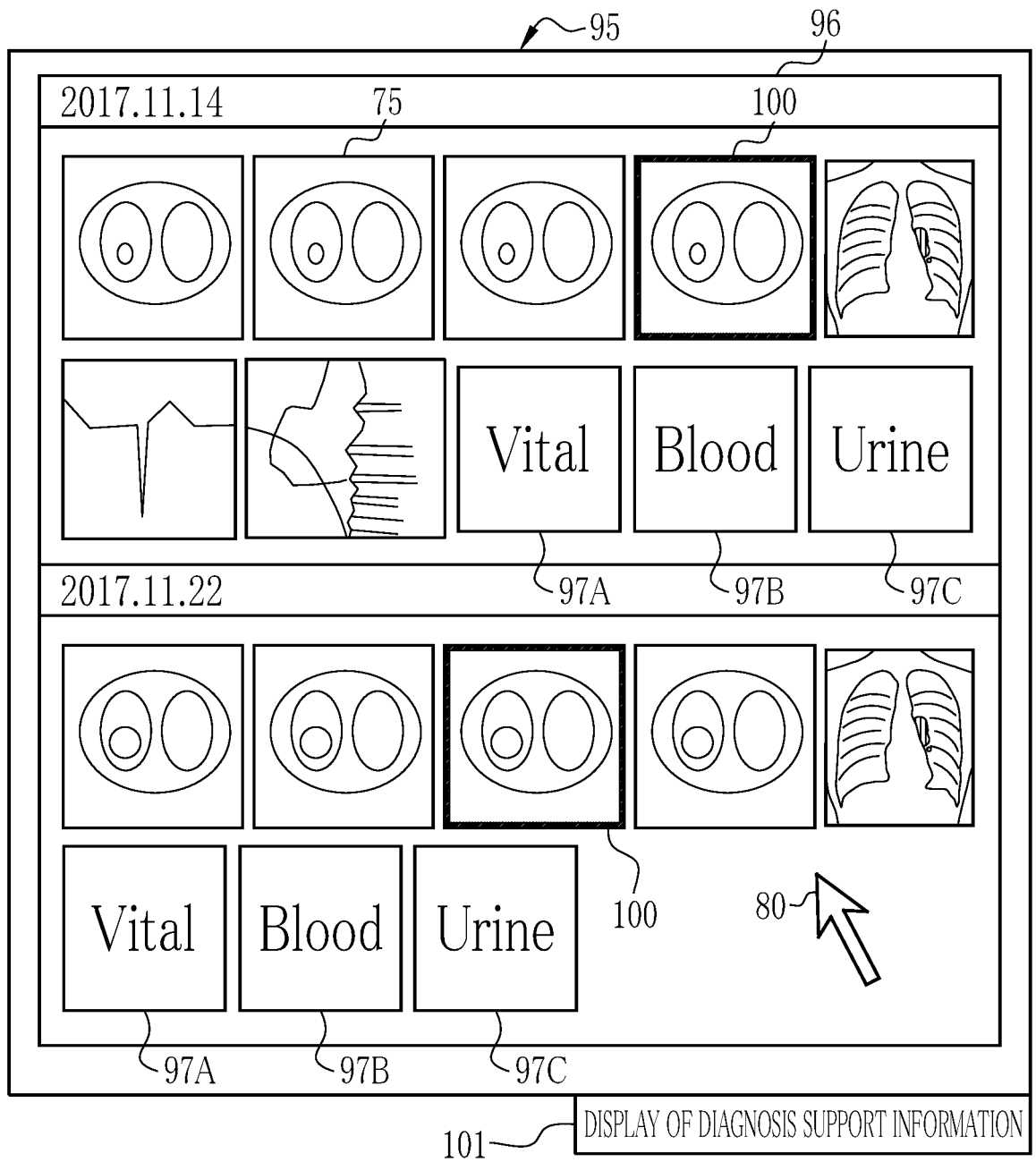
FIG. 15 is a diagram illustrating an information display screen in a case where selection instructions of at least two pieces of examination data are received and diagnosis support information is output.

FIG. 15 illustrates the information display screen 95 in a case where at least two of the thumbnails 75 and the icons 97A to 97C in the list display region 96 are selected by the cursor 80, that is, in a case where the selection instructions of at least two pieces of examination data are performed. At this time, in a case where the suitable diagnosis support algorithm 30C according to the at least two pieces of examination data of which the selection instructions are received is selected by the algorithm selection unit 62, and the diagnosis support information of the suitable diagnosis support algorithm 30C is output from the analysis processing unit 63, a display switching tab 101 for displaying the diagnosis support information appears below the information display screen 95.

Figure 16:
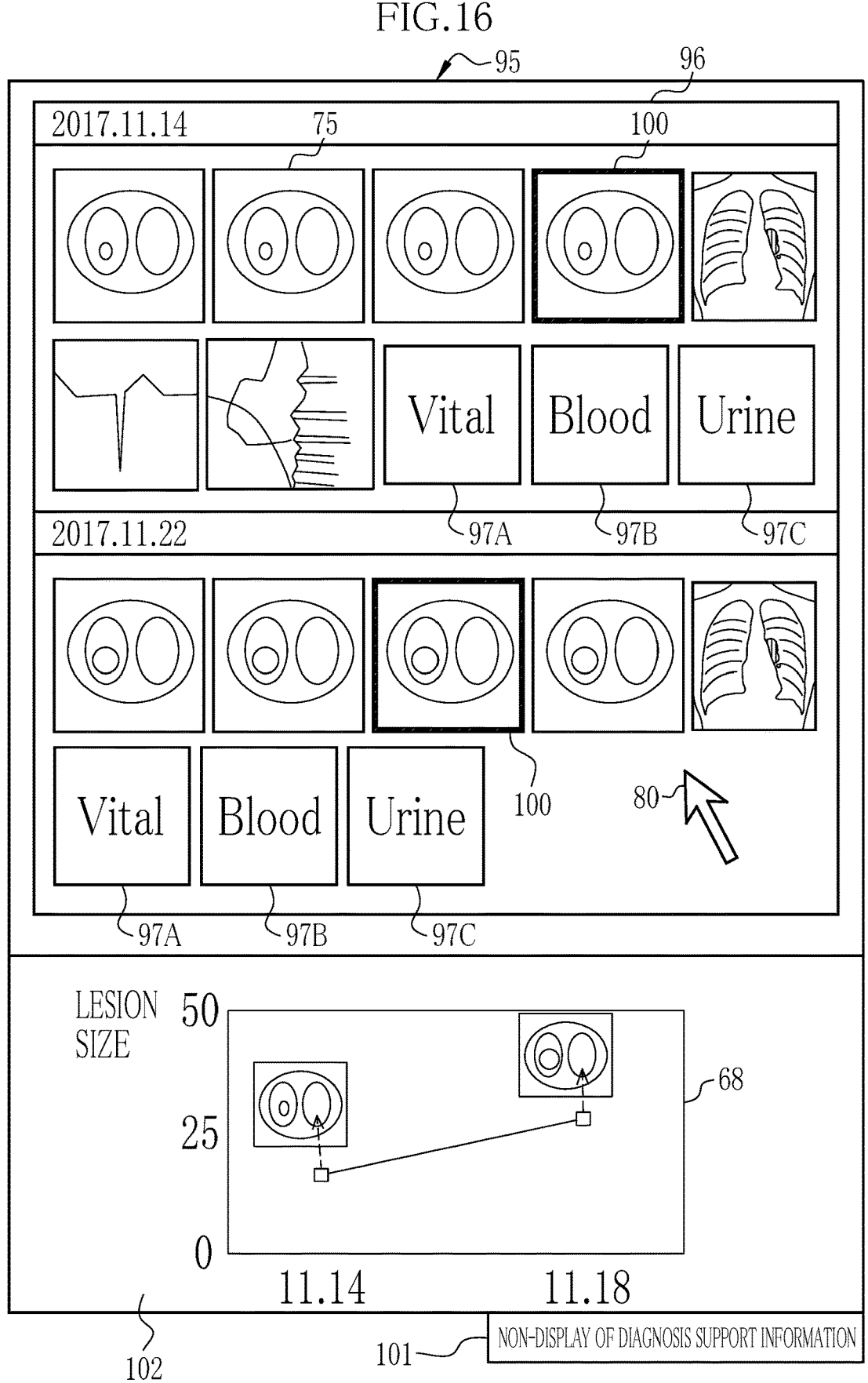
FIG. 16 is a diagram illustrating an information display screen in which an information display region is displayed.

In a case where the display switching tab 101 is selected by the cursor 80, the screen output control unit 65 causes an information display region 102 to be displayed below the list display region 96 as illustrated in FIG. 16. The information display region 102 displays the diagnosis support information of the suitable diagnosis support algorithm 30C. Similar to the case of FIG. 10, FIG. 16 illustrates a case where thumbnails 75 of two CT images having different imaging date and time are selected by the cursor 80, and the lesion size change graph 68 is output as the diagnosis support information.

In a case where the display switching tab 101 is selected again by the cursor 80 in a state illustrated in FIG. 16 where the information display region 102 is displayed, the screen output control unit 65 returns the information display screen 95 to a state illustrated in FIG. 15 where the information display region 102 is not displayed. That is, the screen output control unit 65 switches between display and non-display of the information display region 102 according to the doctor's operation on the display switching tab 101. The selection instruction of the display switching tab 101 is also included in the editing instruction.

The algorithm selection unit 62 selects again the suitable diagnosis support algorithm 30C each time the selection state of the examination data in the list display region 96 is changed. In a case where the suitable diagnosis support algorithm 30C is selected again by the algorithm selection unit 62 so that the diagnosis support information is updated, the screen output control unit 65 switches the display of the information display region 102 to the updated diagnosis support information in conjunction with the change of the selection state.

A more specific example will be described using FIGS. 17A to 18B. FIG. 17A illustrates the information display screen 95 illustrated in FIG. 16, and FIG. 18A illustrates contents of the selection instruction, the suitable diagnosis support algorithm 30C, and the diagnosis support information of the information display screen 95 illustrated in FIG. 16. That is, in the information display screen 95 illustrated in FIG. 16, the thumbnails 75 of two CT images having different imaging date and time are selected, the diagnosis support algorithm 30 having the algorithm ID "AL001" is selected as the suitable diagnosis support algorithm 30C, and the lesion size change graph 68 is displayed as the diagnosis support information.

Figure 17B:
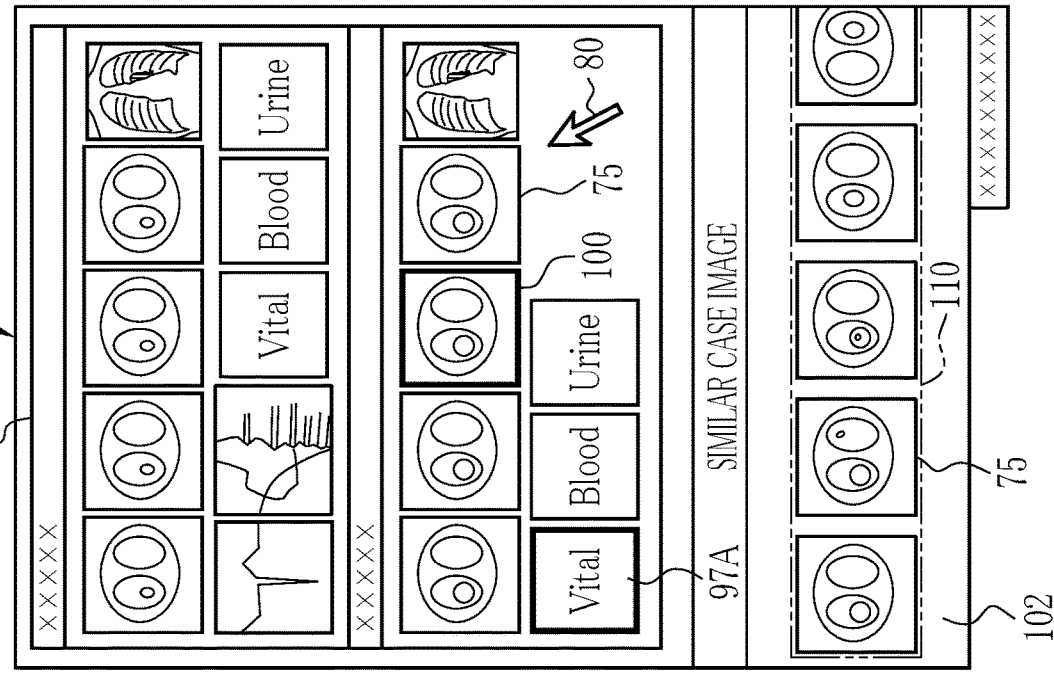
FIGS. 17A and 17B are diagrams illustrating an aspect in which, in a case where a suitable diagnosis support algorithm is selected again so that diagnosis support information is updated each time a selection state of the examination data in a list display region is changed, the display of the information display region is switched to the updated diagnosis support information in conjunction with the change of the selection state.
Figure 17A:
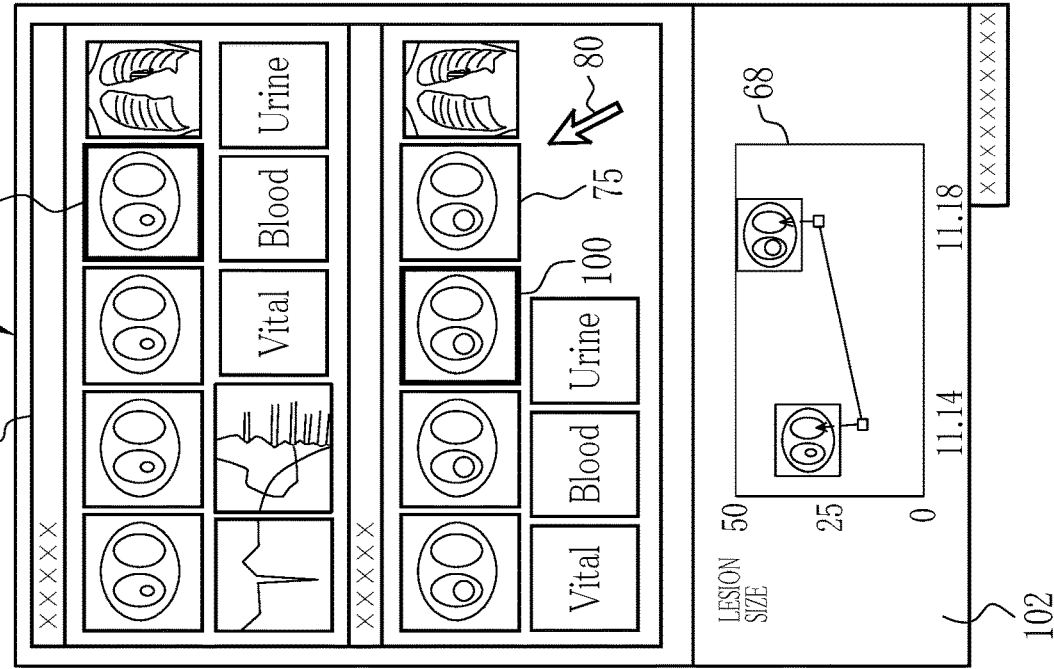
Figure 18A:
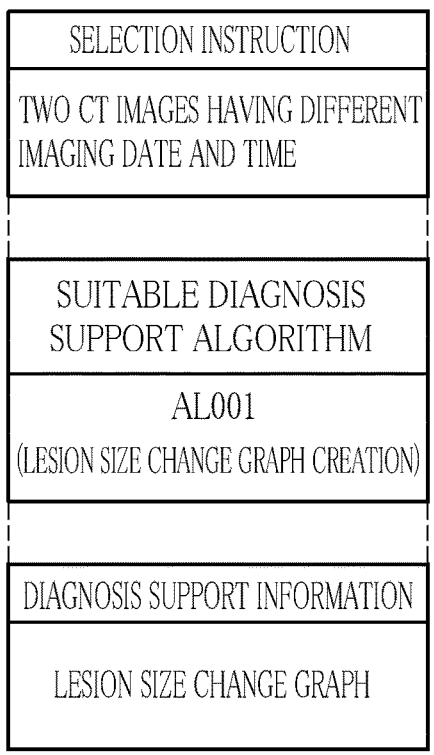
FIGS. 18A and 18B are diagrams illustrating a selection instruction, a suitable diagnosis support algorithm, and contents of diagnosis support information in the information display screen illustrated in FIGS. 17A and 17B, FIG. 18A corresponds to FIG. 17A, and FIG. 18B corresponds to FIG. 17B.
Figure 18B:
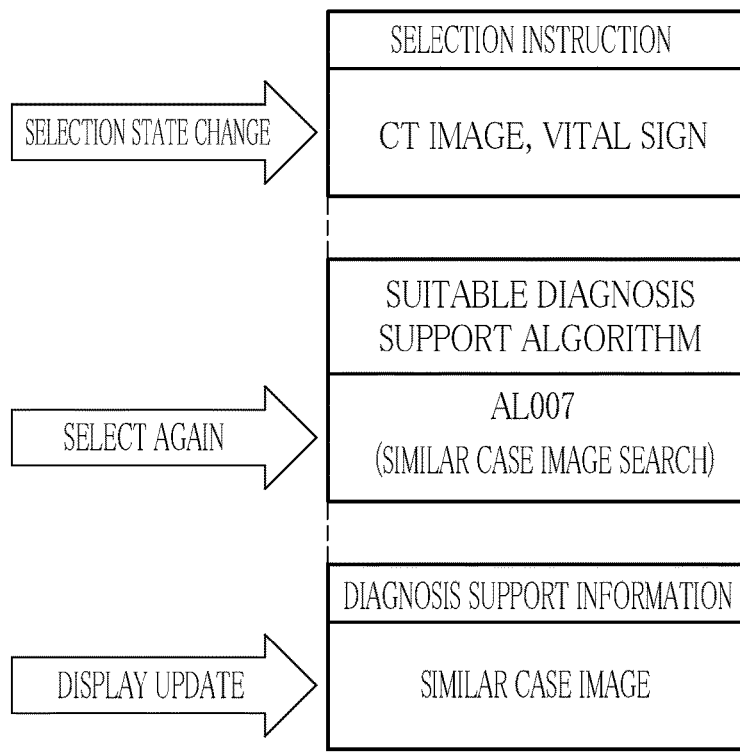

In a case where the selection state of the examination data in the list display region 96 is changed from this state to the thumbnail 75 of one CT image (any one medical image) and the icon 97A corresponding to the vital sign as illustrated in FIGS. 17B and 18B, the algorithm selection unit 62 selects again the suitable diagnosis support algorithm 30C from the diagnosis support algorithm 30 having the algorithm ID "AL001" to the diagnosis support algorithm 30 having an algorithm ID "AL007".

According to the algorithm correspondence table 56 illustrated in FIG. 9, the diagnosis support algorithm 30 having the algorithm ID "AL007" is for search of a similar case image. Therefore, similar case images are output as the diagnosis support information. The screen output control unit 65 causes a list 110 of thumbnails 75 of the searched similar case images to be displayed on the information display region 102, instead of the lesion size change graph 68. A case in which the states of FIGS. 17B and 18B are later than the states of FIGS. 17A and 18A has been described, but a case in which the states of FIGS. 17B and 18B are earlier than the states of FIGS. 17A and 18A is satisfied only by reversing the direction of the arrow.

In a case where a plurality of diagnosis support algorithms 30 are registered for the same set of examination data, such as the diagnosis support algorithms 30 having the algorithm IDs "AL002" and "AL003", all of the plurality of diagnosis support algorithms 30 are selected as the suitable diagnosis support algorithm 30C. Therefore, in the information display region 102, all of pieces of the diagnosis support information of the plurality of diagnosis support algorithms 30 are displayed.

In a case where the number of the thumbnails 75 and the icons 97A to 97C reach a number that cannot be displayed at one time in the list display region 96, a vertical scroll bar is displayed in the list display region 96. Similarly, even in a case where the diagnosis support information cannot be displayed at one time in the information display region 102, a vertical scroll bar is displayed in the information display region 102.

Hereinafter, the operation of the above configuration will be described with reference to the flowcharts in FIGS. 19 and 20. First, the medical staff such as a doctor accesses the medical examination support server 12 via the client terminal 11, and performs authentication. In this case, the medical staff inputs his/her own staff ID and an authentication key. After authentication, in the medical examination support server 12, the request receiving unit 60 receives various requests from the client terminal 11.

Figure 19:
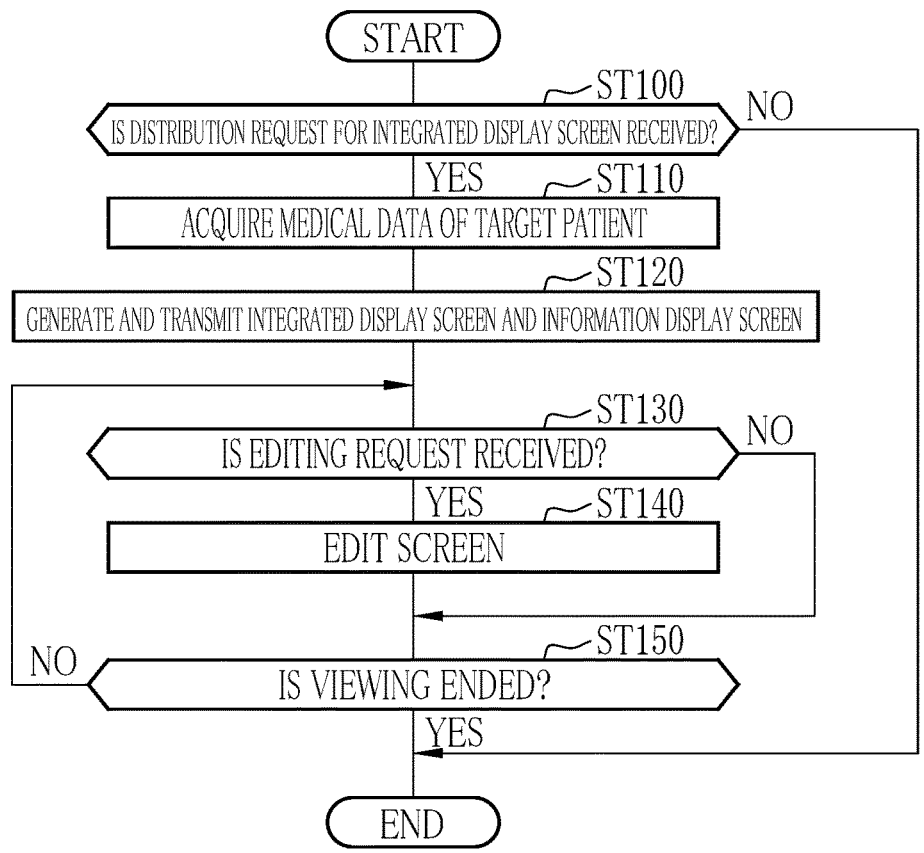
FIG. 19 is a flowchart illustrating a processing procedure of a medical examination support server.

In FIG. 19, in a case where the distribution request for the integrated display screen 35 is received by the request receiving unit 60 (YES in step ST100), an acquisition request for the medical data of the target patient is issued from the medical data acquisition unit 61 to the server group 14. The medical data of the target patient transmitted from the server group 14 in response to the acquisition request is acquired by the medical data acquisition unit 61 (step ST110).

The medical data of the target patient is output from the medical data acquisition unit 61 to the screen output control unit 65. In the screen output control unit 65, the integrated display screen 35 and the information display screen 95 are generated on the basis of the medical data of the target patient from the medical data acquisition unit 61. The generated integrated display screen 35 and information display screen 95 are transmitted to the client terminal 11 which is a request source of the distribution request (step ST120).

In the client terminal 11 which is a request source of the distribution request for the integrated display screen 35, the integrated display screen 35 and the information display screen 95 from the medical examination support server 12 are displayed on the display 23. In this display state, an editing instruction such as selecting a window in the second display region 71 by the cursor 80 is performed by the medical staff. In this manner, an editing request is issued from the browser control unit 51.

The editing request is received by the request receiving unit 60 (YES in step ST130). Then, screen editing according to the contents of the editing request is performed by the screen output control unit 65 (step ST140). For example, in a case where a window in which the thumbnail 75 is displayed in the second display region 71 is selected by the cursor 80, the viewer screen 85 is displayed in a pop-up on the integrated display screen 35. The processing of steps ST130 and ST140 is repeatedly performed until viewing of the integrated display screen 35 and the information display screen 95 is ended (YES in step ST150).

Figure 20:
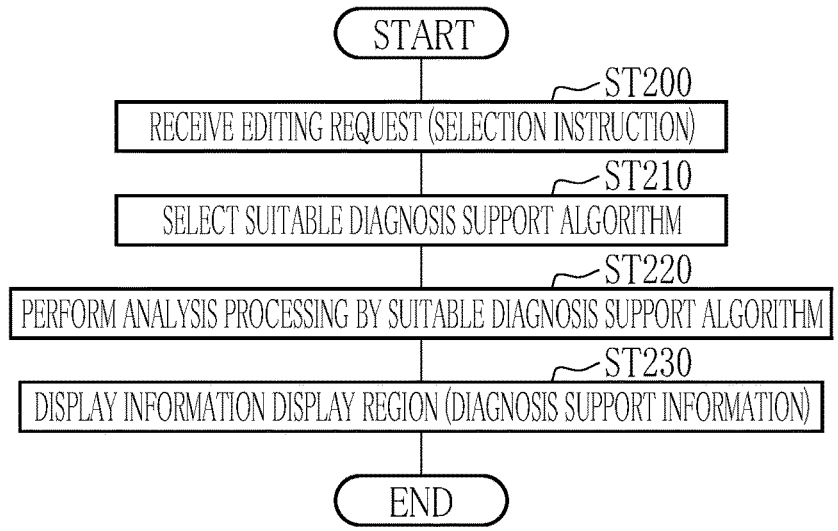
FIG. 20 is a flowchart illustrating a processing procedure of a medical examination support server.

FIG. 20 illustrates a case where there are selection instructions of at least two pieces of examination data in the list display region 96 of the information display screen 95 and an editing request including information of the at least two pieces of examination data is received by the request receiving unit 60 (step ST200, instruction receiving step). In this case, as indicated in step ST210, a suitable diagnosis support algorithm 30C according to the at least two pieces of examination data is selected from among a plurality of diagnosis support algorithms 30 by the algorithm selection unit 62 (algorithm selection step).

The suitable diagnosis support algorithm 30C is transferred from the information management unit 64 to the analysis processing unit 63. In the analysis processing unit 63, analysis processing by the suitable diagnosis support algorithm 30C is performed, and diagnosis support information of the suitable diagnosis support algorithm 30C is output (step ST220, analysis processing step). The diagnosis support information of the suitable diagnosis support algorithm 30C is transferred from the analysis processing unit 63 to the screen output control unit 65.

After the diagnosis support information of the suitable diagnosis support algorithm 30C is output, the display switching tab 101 is displayed below the information display screen 95 by the screen output control unit 65 as illustrated in FIG. 15. In a case where the display switching tab 101 is selected by the cursor 80, the information display region 102 is displayed (step ST230, screen output control step) by the screen output control unit 65 as illustrated in FIG. 16. In a case where the display switching tab 101 is selected again by the cursor 80 in a state where the information display region 102 is displayed, the information display region 102 is not displayed by the screen output control unit 65.

In a case where the selection state of the examination data in the list display region 96 is changed, the processing returns. That is, as illustrated in FIGS. 17A to 18B, the suitable diagnosis support algorithm is selected again by the algorithm selection unit 62, and the display of the information display region 102 is switched to the updated diagnosis support information by the screen output control unit 65.

In the medical examination support server 12, among a plurality of pieces of examination data obtained in the medical examination performed on the patient, selection instructions of at least two pieces of examination data are received by the request receiving unit 60, and a suitable diagnosis support algorithm 30C according to the at least two pieces of examination data is selected from among the plurality of diagnosis support algorithms 30 by the algorithm selection unit 62. Accordingly, it is possible to select a suitable diagnosis support algorithm 30C for a plurality of pieces of examination data without the intervention of a doctor.

The diagnosis support information of the suitable diagnosis support algorithm 30C is displayed in the information display region 102 of the information display screen 95 by the screen output control unit 65. Therefore, it is possible for the doctor to easily check the diagnosis support information.

The selection of the thumbnails 75 or the icons 97A to 97C in the list display region 96 is intended only to display the viewer screen 85 or the screen in which the measurement values of all of the measurement items are displayed during the diagnosis work, and is not for instructing the display of diagnosis support information. However, in a case where the thumbnails 75 or the icons 97A to 97C in the list display region 96 are selected, in the background, the medical examination support server 12 automatically performs selection of a suitable diagnosis support algorithm 30C, the analysis processing, and the like, and further automatically displays the diagnosis support information. Therefore, it is possible for the doctor to obtain the diagnosis support information by simply proceeding with the diagnosis work naturally without tending to instruct the display of the diagnosis support information.

In a case where the suitable diagnosis support algorithm 30C is selected again by the algorithm selection unit 62 so that the diagnosis support information is updated each time the selection state of the examination data in the list display region 96 is changed, the display of the information display region 102 is switched to the updated diagnosis support information by the screen output control unit 65 in conjunction with the change of the selection state, and therefore it is possible to always provide the diagnosis support information suitable for a situation of the diagnosis work to the doctor.

In a case where a selection instruction of one piece of examination data is received, the detailed information of the one piece of examination data is displayed by the screen output control unit 65, and therefore, it is possible to check the details of the examination data which cannot be known from the thumbnails 75 and the icons 97A to 97C.

In some cases, the doctor makes a diagnosis without referring to the diagnosis support information. For such a doctor, the display of the information display region 102 is just troublesome. Therefore, in the embodiment, display and non-display of the information display region 102 is switched according to the doctor's operation by the screen output control unit 65. In doing so, it is preferable that the doctor who does not require the diagnosis support information does not feel bothered. Further, since the information display region 102 is displayed by one action such as selecting the display switching tab 101 by the cursor 80, the doctor who requires the diagnosis support information also has minimal stress.

Second Embodiment

Figure 22:
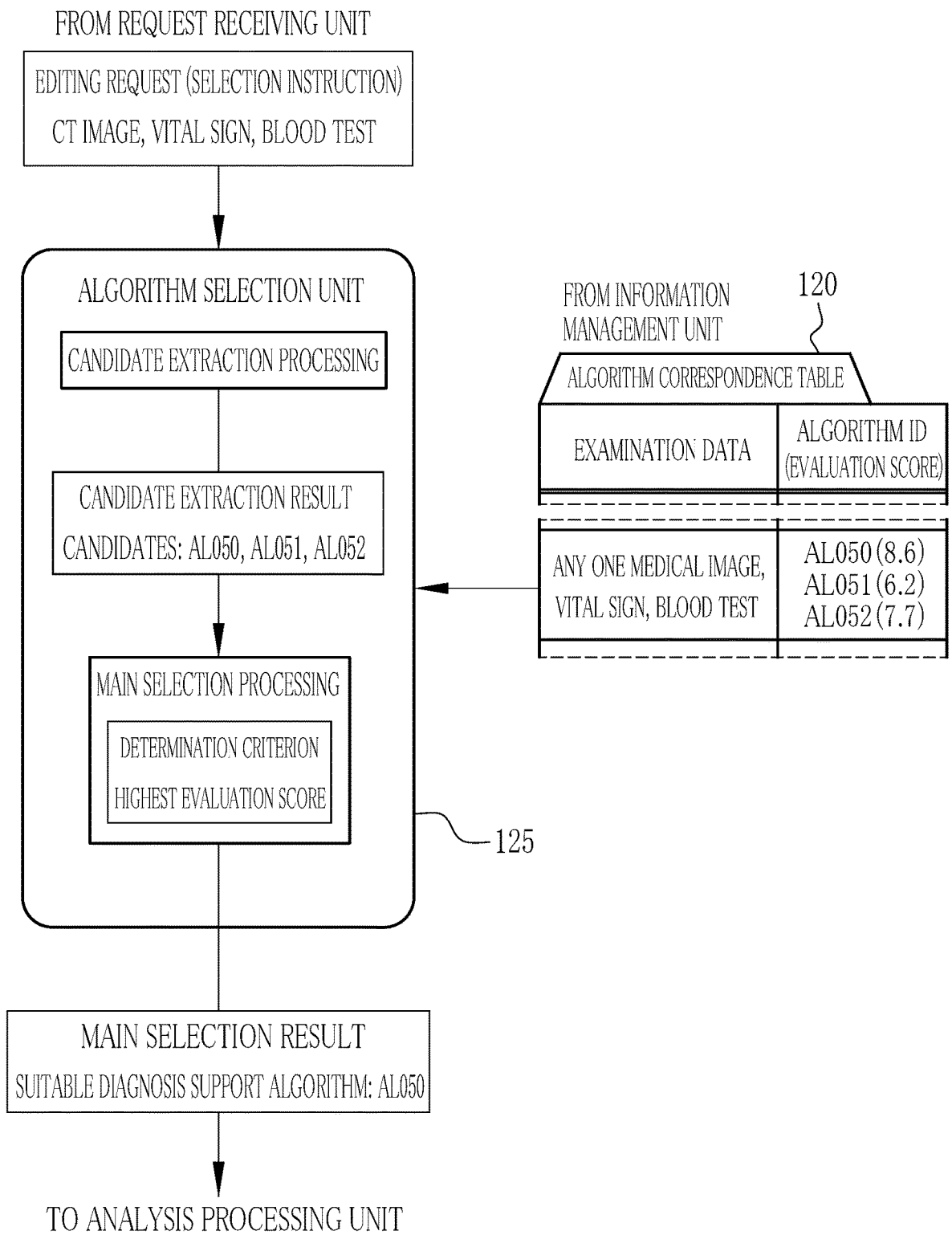
FIG. 22 is a diagram illustrating the second embodiment in which selection of a suitable diagnosis support algorithm is performed by two stages.
Figure 23:
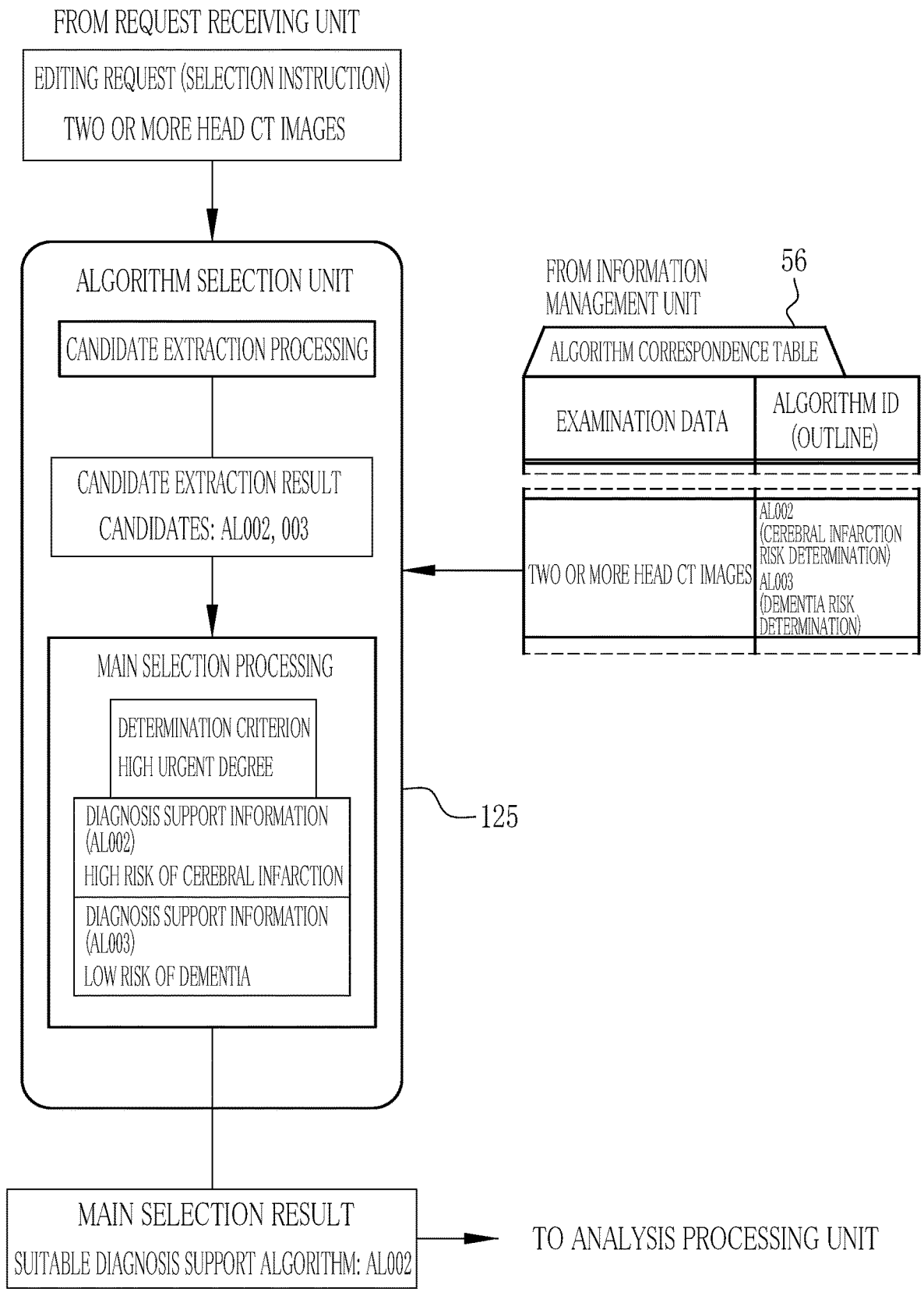
FIG. 23 is a diagram illustrating another example of the second embodiment in which selection of a suitable diagnosis support algorithm is performed by two stages.

In the second embodiment illustrated in FIGS. 21 to 23, selection of a suitable diagnosis support algorithm 30C is performed by two stages.

In FIG. 21, an algorithm correspondence table 120 of the embodiment has an item of an evaluation score. The evaluation score is an average value of values that the doctor inputs on a comprehensive evaluation site of the diagnosis support algorithm 30 established on the web, and has a perfect score of 10.

FIG. 21 illustrates an example in which for the examination data of "any one medical image, vital sign, and blood test", three algorithm IDs, an algorithm ID "AL050", "AL051", and "AL052" (each of which the outline is similar case image search) are registered. Regarding the evaluation score, the algorithm ID "AL050" has the highest score of "8.6", and the algorithm ID "AL052" having a score of "7.7" and the algorithm ID "AL051" having a score of "6.2" follow in this order.

In FIG. 22, an algorithm selection unit 125 of the embodiment performs candidate extraction processing and main selection processing. The candidate extraction processing is processing of extracting candidates for the suitable diagnosis support algorithm 30C according to the at least two pieces of examination data of which the selection instructions are received by the request receiving unit 60. The candidate extraction processing is the same as the processing of selecting the suitable diagnosis support algorithm 30C performed by the algorithm selection unit 62 in the first embodiment.

The main selection processing is processing of selecting a suitable diagnosis support algorithm 30C from among candidates extracted in the candidate extraction processing, according to a determination criterion set in advance. A suitable diagnosis support algorithm 30C which is to be used finally is selected in the main selection processing. Therefore, it can be said that the candidate extraction processing is temporary selection processing of selecting temporarily a suitable diagnosis support algorithm 30C.

FIG. 22 illustrates a case where the at least two pieces of examination data of which the selection instructions are received by the request receiving unit 60 are a CT image (any one medical image), a vital sign, and a blood test. In this case, the algorithm selection unit 125 refers to the algorithm correspondence table 120 from the information management unit 64, and extracts the algorithm IDs "AL050", "AL051", and "AL052" of a case where the examination data is "any one medical image, vital sign, and blood test" (candidate extraction processing).

Next, the algorithm selection unit 125 selects the algorithm ID "AL050" having the highest evaluation score from among algorithm IDs "AL050", "AL051", and "AL052" according to the determination criterion of "highest evaluation score" (main selection processing). The algorithm selection unit 125 outputs the selected algorithm ID "AL050" to the analysis processing unit 63 as the main selection result. Since the subsequent processing is the same as that of the first embodiment, the description thereof is omitted.

In a case where there is only one candidate extracted in the candidate extraction processing, there is no need to further narrow down candidates, and thus naturally, the main selection processing is not performed.

A questionnaire for causing doctors to select whether diagnosis support information was helpful for diagnosis is displayed on the information display region 102, and the result of statistical analysis of the questionnaire result may be used as the evaluation score. The determination criterion is not limited to the "highest evaluation score" exemplified above. The determination criterion may be "evaluation score threshold value or greater" or the like.

Further, the determination criterion may not be related to the evaluation score. For example, as illustrated in FIG. 23, an urgent degree which is a degree of necessity for informing the doctor of the diagnosis support information may be used as the determination criterion, and from among the candidates, a diagnosis support algorithm having a high urgent degree may be selected in the main selection processing.

FIG. 23 illustrates a case in which the algorithm correspondence table is the algorithm correspondence table 56 illustrated in FIG. 9 of the first embodiment and the at least two pieces of examination data of which the selection instructions are received by the request receiving unit 60 are two or more head CT images. In this case, the algorithm selection unit 125 refers to the algorithm correspondence table 56, and extracts the algorithm IDs "AL002 (cerebral infarction risk determination)" and "AL003 (dementia risk determination) of a case where the examination data is "two or more head CT images".

Here, in a case where the diagnosis support information of the diagnosis support algorithm 30 having the algorithm ID "AL002" is "high risk of cerebral infarction", the diagnosis support information of the diagnosis support algorithm 30 having the algorithm ID "AL003" is "low risk of dementia", and the determination criterion is a "high urgent degree", the algorithm selection unit 125 selects the algorithm ID "AL002" considered to have a relatively high urgent degree from among the algorithm IDs "AL002" and "AL003". The algorithm selection unit 125 outputs the selected algorithm ID "AL002" to the analysis processing unit 63 as the main selection result. In this case, the screen output control unit 65 unconditionally displays the information display region 102, instead of displaying the information display region 102 with the selection of the display switching tab 101 as in the first embodiment.

In this manner, in a case where from among the candidates, a diagnosis support algorithm having a relatively high urgent degree is selected in the main selection processing by using the urgent degree as the determination criterion, it is possible to reliably inform the doctor of the diagnosis support information with a higher urgent degree. Further, in a situation illustrated in FIG. 23, in a case where the doctor is performing the diagnosis work by suspecting dementia, since the doctor is informed that the risk of cerebral infarction that the doctor has not suspected is high, it is possible to give new notice to the doctor, which is effective in preventing oversight of diseases.

Note that the level of the urgent degree may be determined according to the diseases handled by the diagnosis support algorithm 30. For example, in a case where a diagnosis support algorithm 30 for determining a morbidity risk of emphysema and a diagnosis support algorithm 30 for determining a morbidity risk of lung cancer are extracted as candidates and the diagnosis support information of both the diagnosis support algorithms 30 is "risk high", a diagnosis support algorithm 30 for determining a morbidity risk of lung cancer considered to have a higher urgent degree than emphysema is selected as the suitable diagnosis support algorithm 30C.

The information display screen 95 may not always be displayed together with the integrated display screen 35. In a case where the distribution request for the information display screen 95 is received by the request receiving unit 60 separately from the distribution request for the integrated display screen 35, the information display screen 95 may be displayed in a pop-up on the integrated display screen 35.

In addition to the thumbnails 75, the icons 97A to 97C, and the diagnosis support information, a manual operation log which is a history of a manual operation of the medical staff may be displayed on the information display screen 95. The manual operation log includes specifically, selecting a window in the second display region 71 to display the viewer screen 85, and selecting the icon 97A to display the screen in which the measurement values of all of the measurement items of the vital signs are displayed.

The hardware configuration of a computer which constitutes the medical examination support server 12 corresponding to the medical examination support apparatus of the invention can be modified in various ways. For example, in order to improve the processing capacity and reliability, the medical examination support server 12 may be constituted by a plurality of server computers that are separated from each other as hardware. For example, the functions of the request receiving unit 60, the medical data acquisition unit 61, and the analysis processing unit 63, and the functions of the algorithm selection unit 62, the information management unit 64, and the screen output control unit 65 are distributed to two server computers. In this case, the two server computers constitute the medical examination support apparatus.

In each embodiment described above, an aspect in which the medical examination support server 12 generates various display screens and the various display screens are reproduced by the client terminal 11 and displayed on the display 23 on the basis of the screen data of the various display screens from the medical examination support server 12 is exemplified. However, data which is a source for generating various display screens may be transmitted from the medical examination support server 12 to the client terminal 11 and the client terminal 11 may generate the various display screens. In this case, the screen output control unit 65 is constructed in the CPU 42A of the client terminal 11.

Further, each processing unit constructed in the CPU 42B of the medical examination support server 12 may be constructed in the CPU 42A of the client terminal 11, and the client terminal 11 may be operated as the medical examination support apparatus. In this case, the request receiving unit 60 directly receives instructions from the GUI control unit 50 instead of the distribution request or the like. In addition, the screen output control unit 65 outputs the generated various display screens to the GUI control unit 50. Further, the electronic medical record server 15 or the image server 16 may be operated as the medical examination support apparatus.

In this manner, the hardware configuration of a computer can be appropriately changed according to the required performance, such as processing capacity, safety, or reliability. Further, in order to ensure the safety and the reliability, without being limited to hardware, an application program such as the operation program 55 may be duplicated or may be distributed and stored in a plurality of storage devices.

In each embodiment described above, an aspect in which the medical examination support server 12 is used in one medical facility is described, but an aspect in which the medical examination support server 12 is used by a plurality of medical facilities may be adopted.

In each embodiment described above, the medical examination support server 12 is communicably connected to the client terminal 11, which is installed in one medical facility, through the network 13 such as a LAN, and provides various display screens in response to the distribution request from the client terminal 11. In order for the medical examination support server 12 to be used by a plurality of medical facilities, the medical examination support server 12 is communicably connected to each of the client terminals 11 installed in the plurality of medical facilities, for example, through a wide area network (WAN) such as the Internet or a public communication network. Then, the medical examination support server 12 receives the distribution request from each client terminal 11 of the plurality of medical facilities through the WAN, and provides various display screens to each client terminal 11. In case of using the WAN, it is preferable to construct a virtual private network (VPN) or to use a communication protocol with a high security level, such as hypertext transfer protocol secure (HTTPS), in consideration of information security.

In this case, the electronic medical record 19, and the medical image 20 are managed for each medical facility. Further, the installation location and operating entity of the medical examination support server 12 in this case may be a data center operated by a company that is different from the medical facilities, or may be one of the plurality of medical facilities, for example.

It is sufficient that the medical examination support apparatus of the invention has at least the function of controlling the output of the information display screen 95, and thus the medical examination support apparatus of the invention may not necessarily have the function of controlling the output of the integrated display screen 35 as in the screen output control unit 65 in the embodiment described above. Further, it is sufficient that the information display screen 95 has at least the information display region 102, and may not have the list display region 96.

In each embodiment described above, the hardware structure of the processing units executing various kinds of processing, such as the request receiving unit 60, the medical data acquisition unit 61, the algorithm selection unit 62 or 125, the analysis processing unit 63, the information management unit 64, and the screen output control unit 65, is various processors as follows.

The various processors include a CPU, a programmable logic device (PLD), dedicated electrical circuitry, and the like. The CPU is a general-purpose processor functioning as various processing units by executing software (program) as being well known. The PLD is a processor of which the circuit configuration can be changed after manufacture, such as a field programmable gate array (FPGA). The dedicated electrical circuitry is a processor having a circuit configuration designed exclusively to execute specific processing, such as an application specific integrated circuit (ASIC).

One processing unit may be configured by one of the various processors or a combination of the same or different kinds of two or more processors (for example, a combination of a plurality of FPGAs or a combination of a CPU and an FPGA). In addition, a plurality of processing units may be configured by one processor. As an example where a plurality of processing units are configured by one processor, first, there is an aspect where one processor is configured by a combination of one or more CPUs and software, and this processor functions as a plurality of processing units. Second, there is an aspect where a processor fulfilling the functions of the entire system including a plurality of processing units by one IC chip as typified by a system on chip (SoC) or the like is used. In this manner, various processing units are configured by using one or more of the above-described various processors as hardware structures.

Furthermore, the hardware structures of these various processors are more specifically electrical circuitry where circuit elements, such as semiconductor elements, are combined.

From the above description, the medical examination support apparatus described in Additional remark 1 described below can be grasped.

[Additional Remark 1]

A medical examination support apparatus comprising:
an instruction receiving processor that receives at least two selection instructions among a plurality of pieces of examination data obtained in a medical examination performed on a patient;
an algorithm selection processor that selects a suitable diagnosis support algorithm according to the at least two pieces of examination data of which the selection instruction is received by the instruction receiving processor, from among a plurality of diagnosis support algorithms for performing analysis processing on the examination data and outputting an analysis processing result as diagnosis support information for supporting diagnosis of a doctor;
an analysis processing processor that performs the analysis processing by the suitable diagnosis support algorithm; and
a screen output control processor that controls an output of an information display screen including an information display region in which the diagnosis support information of the suitable diagnosis support algorithm is displayed.

In the invention, it is also possible to appropriately combine the above-described various embodiments or various modification examples. Further, without being limited to the embodiments described above, various configurations can be adopted as long as the configurations do not depart from the scope of the invention. In addition to the program, the invention also extends to a storage medium that stores the program.

EXPLANATION OF REFERENCES

10: medical examination system
11: client terminal
12: medical examination support server (medical examination support apparatus)
13: network
14: server group
15: electronic medical record server
15A: medical record database (DB)
16: image server
16A: image database (DB)
19: electronic medical record
20: medical image
23, 44: display
24, 45: input device
30: diagnosis support algorithm
30C: suitable diagnosis support algorithm
35: integrated display screen
40, 40B: storage device
41: memory
42, 42A, 42B: CPU
43: communication unit
46: data bus
50: GUI control unit
51: browser control unit
55: operation program
56, 120: algorithm correspondence table
60: request receiving unit
61: medical data acquisition unit
62, 125: algorithm selection unit
63: analysis processing unit
64: information management unit
65: screen output control unit
68: lesion size change graph
70: first display region
71: second display region
72: third display region
73: fourth display region
75: thumbnail
80: cursor
85: viewer screen
86: image display region
87: information display region
95: information display screen
96: list display region
97A to 97C: icon
100: frame
101: display switching tab
102: information display region
110: list of thumbnails of similar case images
ST100 to ST150, ST200 to ST230: step

What is claimed is:

1. A medical examination support apparatus comprising:
a processor constituting a medical examination support server and configured to function as:
a screen output control unit configured to control an output of an information display screen, the information display screen including a list display region in which thumbnails and icons of a plurality of pieces of examination data obtained in a medical examination performed on a patient are displayed;
an instruction receiving unit that receives at least two selection instructions among the thumbnails and the icons of a plurality of pieces of examination data, the at least two selection instructions comprising selection by control of a cursor of at least two of the thumbnails or at least one of the thumbnails and one of the icons;
an algorithm selection unit that selects a suitable diagnosis support algorithm utilized by the medical examination support server according to at least two pieces of the examination data of which the selection instruction is received by the instruction receiving unit, from among a plurality of diagnosis support algorithms for performing analysis processing on the examination data and outputting an analysis processing result as diagnosis support information for supporting diagnosis of a doctor by accessing the medical examination support server via a client terminal, wherein the medical examination support server inputs the examination data to the suitable diagnosis support algorithm and causes the suitable diagnosis support algorithm to automatically perform the analysis processing on the examination data,
wherein suitableness of the suitable diagnosis support algorithm is determined by the algorithm selection unit based on a predetermined criterion resulted from an evaluation score and an urgent degree of the suitable diagnosis support algorithm, wherein the evaluation score is statistical analysis of result of a questionnaire to the doctors, wherein the questionnaire is causing the doctors to evaluate whether diagnosis support information, which is outputted from a result of the analysis processed by one of the plurality of diagnosis support algorithms, is helpful for diagnosis; and an analysis processing unit that performs the analysis processing by the suitable diagnosis support algorithm, wherein the screen output control unit controls an output of the information display screen including an information display region in which the diagnosis support information of the suitable diagnosis support algorithm is displayed, wherein the diagnosis support information is transferred from the analysis processing unit to the screen output control unit, wherein the information display screen displays the list display region in which the thumbnails and the icons that have been selected are indicated with a frame, and in a case where the suitable diagnosis support algorithm is selected by the algorithm selection unit, which is a display switching tab, and displays, in a case where the display switching tab is selected by the control of the cursor, the information display region, so as to display the diagnosis support information of the suitable diagnosis support algorithm.

2. The medical examination support apparatus according to claim 1, wherein the information display screen includes the list display region in which the plurality of pieces of examination data are displayed in a list for receiving the selection instruction, in addition to the information display region, the algorithm selection unit selects the suitable diagnosis support algorithm again each time a selection state of the examination data in the list display region is changed, and in a case where the suitable diagnosis support algorithm is selected again by the algorithm selection unit so that the diagnosis support information is updated, the screen output control unit switches a display of the information display region to the updated diagnosis support information in conjunction with the change of the selection state.

3. The medical examination support apparatus according to claim 1, wherein the algorithm selection unit performs candidate extraction processing of extracting candidates for the suitable diagnosis support algorithm according to the at least two pieces of examination data, and main selection processing of selecting the suitable diagnosis support algorithm from among the candidates according to a determination criterion set in advance.

4. The medical examination support apparatus according to claim 1, wherein in a case where the instruction receiving unit receives a selection instruction of one piece of the examination data, the screen output control unit displays detailed information of the one pieces of examination data of which the selection instruction is received by the instruction receiving unit.

5. The medical examination support apparatus according to claim 1, wherein the screen output control unit switches between display and non-display of the information display region according to an operation of the doctor.

6. An operation method of a medical examination support apparatus, the operation method comprising:

a screen output control step of controlling an output of an information display screen, the information display screen including a list display region in which thumbnails and icons of a plurality of pieces of examination data obtained in a medical examination performed on a patient are displayed;

an instruction receiving step of receiving at least two selection instructions among the thumbnails and the icons of a plurality of pieces of examination data, the at least two selection instructions comprising selection by control of a cursor of at least two of the thumbnails or at least one of the thumbnails and one of the icons;

an algorithm selection step of selecting a suitable diagnosis support algorithm utilized by a medical examination support server according to at least two pieces of the examination data of which the selection instruction is received in the instruction receiving step, from among a plurality of diagnosis support algorithms for performing analysis processing on the examination data and outputting an analysis processing result as diagnosis support information for supporting diagnosis of a doctor by accessing the medical examination support server via a client terminal, wherein the medical examination support server inputs the examination data to the suitable diagnosis support algorithm and causes the suitable diagnosis support algorithm to automatically perform the analysis processing on the examination data, wherein suitableness of the suitable diagnosis support algorithm is determined by the algorithm selection step based on a predetermined criterion resulted from an evaluation score and an urgent degree of the suitable diagnosis support algorithm, wherein the evaluation score is statistical analysis of result of a questionnaire to the doctors, wherein the questionnaire is causing the doctors to evaluate whether diagnosis support information, which is outputted from a result of the analysis processed by one of the plurality of diagnosis support algorithms, is helpful for diagnosis; and an analysis processing step of performing the analysis processing by the suitable diagnosis support algorithm, wherein the screen output control step of controlling an output of the information display screen including an information display region in which the diagnosis support information of the suitable diagnosis support algorithm is displayed, wherein the diagnosis support information is transferred from the analysis processing unit to a screen output control unit, wherein the information display screen displays the list display region in which the thumbnails and the icons that have been selected are indicated with a frame, and in a case where the suitable diagnosis support algorithm is selected by the algorithm selection unit, which is a display switching tab, and displays, in a case where the display switching tab is selected by the control of the cursor, the information display region, so as to display the diagnosis support information of the suitable diagnosis support algorithm.

7. A non-transitory computer readable medium for storing a computer-executable program for a medical examination support apparatus, the computer-executable program causing a computer to execute:

a screen output control function of controlling an output of an information display screen, the information display screen including a list display region in which thumbnails and icons of a plurality of pieces of examination data obtained in a medical examination performed on a patient are displayed;

an instruction receiving function of receiving at least selection instructions among the thumbnails and the icons of a plurality of pieces of examination data, the at least two selection instructions comprising selection by control of a cursor of at least two of the thumbnails or at least one of the thumbnails and one of the icons;

an algorithm selection function of selecting a suitable diagnosis support algorithm utilized by the medical examination support server according to at least two pieces of the examination data of which the selection instruction is received in the instruction receiving function, from among a plurality of diagnosis support algorithms for performing analysis processing on the examination data and outputting an analysis processing result as diagnosis support information for supporting diagnosis of a doctor by accessing the medical examination support server via a client terminal, wherein the medical examination support server inputs the examination data to the suitable diagnosis support algorithm and causes the suitable diagnosis support algorithm to automatically perform the analysis processing on the examination data, wherein suitableness of the suitable diagnosis support algorithm is determined by the algorithm selection unit based on a predetermined criterion resulted from an evaluation score and an urgent degree of the suitable diagnosis support algorithm;

an analysis processing function of performing the analysis processing by the suitable diagnosis support algorithm, wherein the evaluation score is statistical analysis of result of a questionnaire to the doctors, wherein the questionnaire is causing the doctors to evaluate whether diagnosis support information, which is outputted from a result of the analysis processed by one of the plurality of diagnosis support algorithms, is helpful for diagnosis, wherein the screen output control function of controlling an output of the information display screen including an information display region in which the diagnosis support information of the suitable diagnosis support algorithm is displayed, wherein the diagnosis support information is transferred from the analysis processing unit to a screen output control unit, wherein the information display screen displays the list display region in which the thumbnails and the icons that have been selected are indicated with a frame, and in a case where the suitable diagnosis support algorithm is selected by the algorithm selection unit, which is a display switching tab, and displays, in a case where the display switching tab is selected by the control of the cursor, the information display region, so as to display the diagnosis support information of the suitable diagnosis support algorithm.

* * * * *